US012642968B2

(12) United States Patent
Wolf, II

(10) Patent No.: US 12,642,968 B2
(45) Date of Patent: *Jun. 2, 2026

(54) APPARATUS AND METHOD FOR INCORPORATION OF OPTICAL SENSING INTO NEUROSTIMULATION SYSTEMS

(71) Applicant: Wavegate Corporation, Lake Charles, LA (US)

(72) Inventor: Erich W. Wolf, II, Lake Charles, LA (US)

(73) Assignee: Wavegate Corporation, Lake Charles, LA (US)

( * ) Notice: Subject to any disclaimer, the term of this patent is extended or adjusted under 35 U.S.C. 154(b) by 1221 days.

This patent is subject to a terminal disclaimer.

(21) Appl. No.: 17/456,828

(22) Filed: Nov. 29, 2021

(65) Prior Publication Data

US 2022/0080203 A1     Mar. 17, 2022

Related U.S. Application Data

(63) Continuation-in-part of application No. 15/879,415, filed on Jan. 24, 2018, now Pat. No. 11,185,706.

(60) Provisional application No. 62/449,933, filed on Jan. 24, 2017.

(51) Int. Cl.

| | |
|---|---|
| *A61N 1/375* | (2006.01) |
| *A61B 17/34* | (2006.01) |
| *A61N 1/05* | (2006.01) |
| *A61N 1/36* | (2006.01) |
| *A61B 5/00* | (2006.01) |
| *A61B 17/32* | (2006.01) |

(52) U.S. Cl.
CPC ...... *A61N 1/36128* (2013.01); *A61B 17/3468* (2013.01); *A61N 1/0553* (2013.01); *A61N 1/36062* (2017.08); *A61N 1/3752* (2013.01); *A61B 5/0086* (2013.01); *A61B 2017/320056* (2013.01); *A61B 2562/0233* (2013.01)

(58) Field of Classification Search
CPC .. A61N 1/3758; A61N 1/0551; A61N 1/0553; A61N 1/36071
See application file for complete search history.

(56) References Cited

U.S. PATENT DOCUMENTS

| | | | |
|---|---|---|---|
| 6,011,993 A | 1/2000 | Tziviskos et al. | |
| 6,324,428 B1 | 11/2001 | Weinberg et al. | |
| 7,742,817 B2 | 6/2010 | Malinowski et al. | |
| 8,543,213 B2 | 9/2013 | Wolf, II | |
| 9,132,273 B2 | 9/2015 | Wolf, II | |
| 9,550,063 B2 | 1/2017 | Wolf, II | |
| 9,656,097 B2 | 5/2017 | Wolf, II | |
| 9,821,161 B2 | 11/2017 | Wolf, II | |
| 10,035,019 B2 | 7/2018 | Wolf, II | |
| 11,185,706 B2 * | 11/2021 | Wolf, II | H05K 1/144 |
| 2009/0202202 A1 | 8/2009 | Lee et al. | |
| 2013/0317573 A1 | 11/2013 | Zhu et al. | |

* cited by examiner

*Primary Examiner* — Joseph M Dietrich
(74) *Attorney, Agent, or Firm* — Schultz & Associates, P.C.

(57) ABSTRACT

A connector system is provided for a positional sensitive spinal cord stimulation apparatus using reflectometry which incorporates the ability to connect to current IPG's either in a percutaneous or laminectomy form and which utilizes a novel light to frequency converter to generate a stimulation voltage in wave form to effect spinal cord stimulation.

16 Claims, 17 Drawing Sheets

200

300

312  302  310

304  306

308

450

452

468
462  472  470

454

456

458

466

474
460

464

PERCUTANEOUS
CONNECTOR
CIRCUIT
800

(PERCUTANEOUS LEAD)

LAMINECTOMY
CONNECTOR CIRCUIT
1200
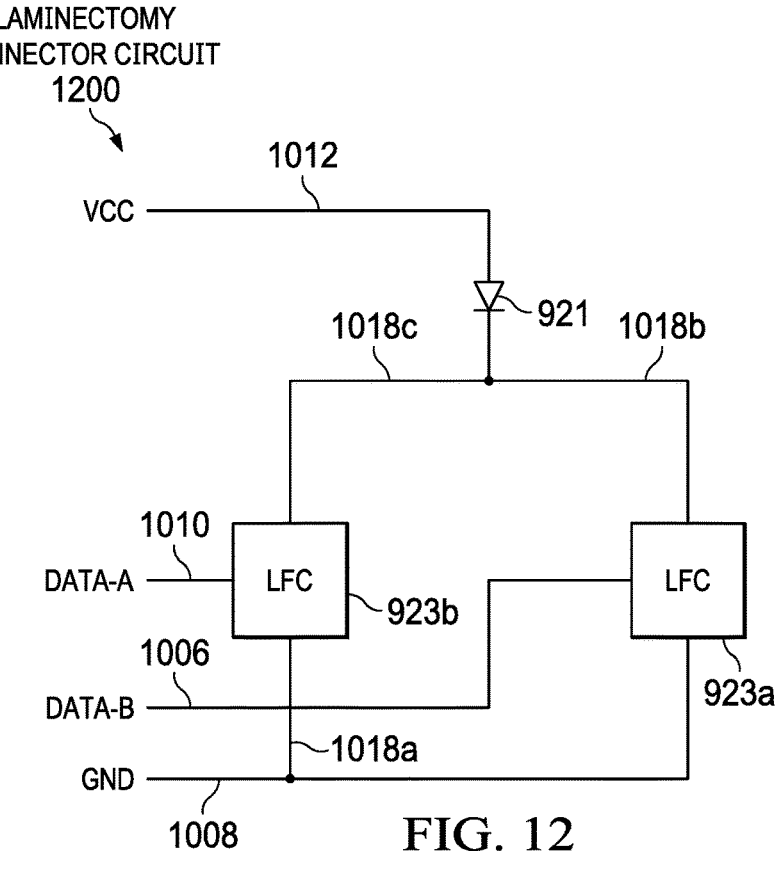
FIG. 12
PROCESSOR
STATE CHART
1300
RUN STATE
1304
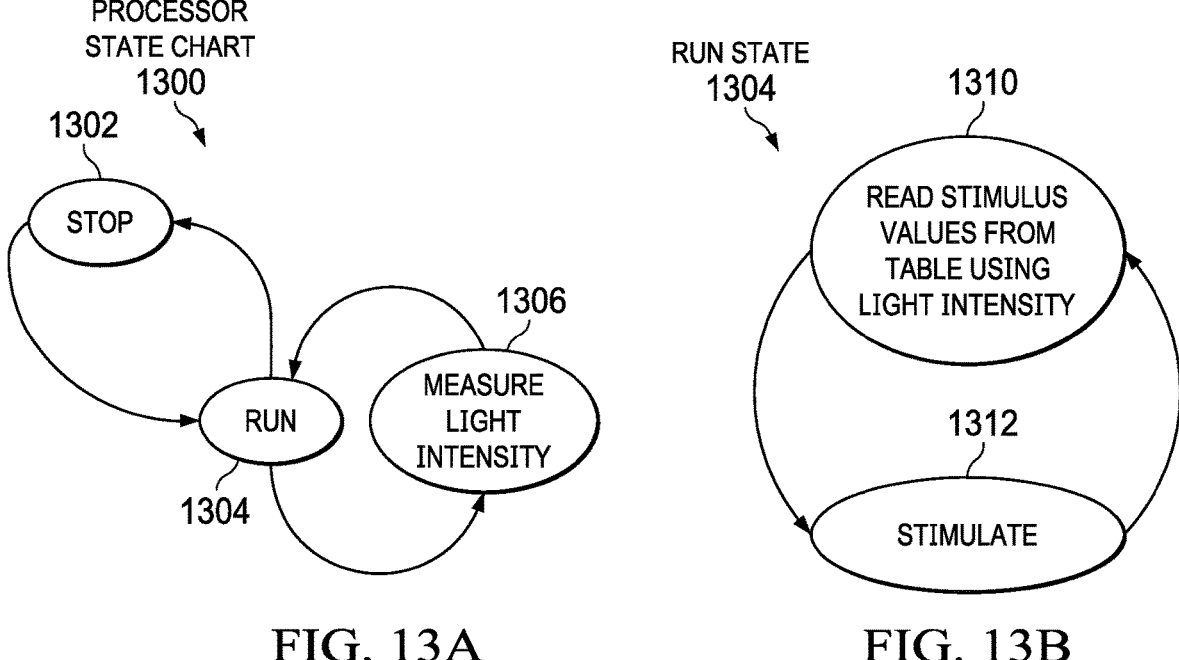
FIG. 13A            FIG. 13B

MEASURE LIGHT
INTENSITY
1306

1500

| LIGHT INTENSITY A | ELECTRODE VOLTAGE/ WAVEFORM $E_1$ | $E_2$ | $E_3$ | $E_4$ | $E_5$ | $E_6$ |
|---|---|---|---|---|---|---|
| 1 | $V_1 / W_1$ | $V_2 / W_2$ | $V_3 / W_3$ | $V_4 / W_4$ | $V_5 / W_5$ | $V_6 / W_6$ |
| 2 | $V_1 / W_1$ | $V_2 / W_2$ | $V_3 / W_3$ | $V_4 / W_4$ | $V_5 / W_5$ | $V_6 / W_6$ |
| 3 | $V_1 / W_1$ | $V_2 / W_2$ | $V_3 / W_3$ | $V_4 / W_4$ | $V_5 / W_5$ | $V_6 / W_6$ |
| 4 | $V_1 / W_1$ | $V_2 / W_2$ | $V_3 / W_3$ | $V_4 / W_4$ | $V_5 / W_5$ | $V_6 / W_6$ |
| 5 | $V_1 / W_1$ | $V_2 / W_2$ | $V_3 / W_3$ | $V_4 / W_4$ | $V_5 / W_5$ | $V_6 / W_6$ |
| 6 | $V_1 / W_1$ | $V_2 / W_2$ | $V_3 / W_3$ | $V_4 / W_4$ | $V_5 / W_5$ | $V_6 / W_6$ |
| 7 | $V_1 / W_1$ | $V_2 / W_2$ | $V_3 / W_3$ | $V_4 / W_4$ | $V_5 / W_5$ | $V_6 / W_6$ |
| 8 | $V_1 / W_1$ | $V_2 / W_2$ | $V_3 / W_3$ | $V_4 / W_4$ | $V_5 / W_5$ | $V_6 / W_6$ |
| 9 | $V_1 / W_1$ | $V_2 / W_2$ | $V_3 / W_3$ | $V_4 / W_4$ | $V_5 / W_5$ | $V_6 / W_6$ |
| 10 | $V_1 / W_1$ | $V_2 / W_2$ | $V_3 / W_3$ | $V_4 / W_4$ | $V_5 / W_5$ | $V_6 / W_6$ |

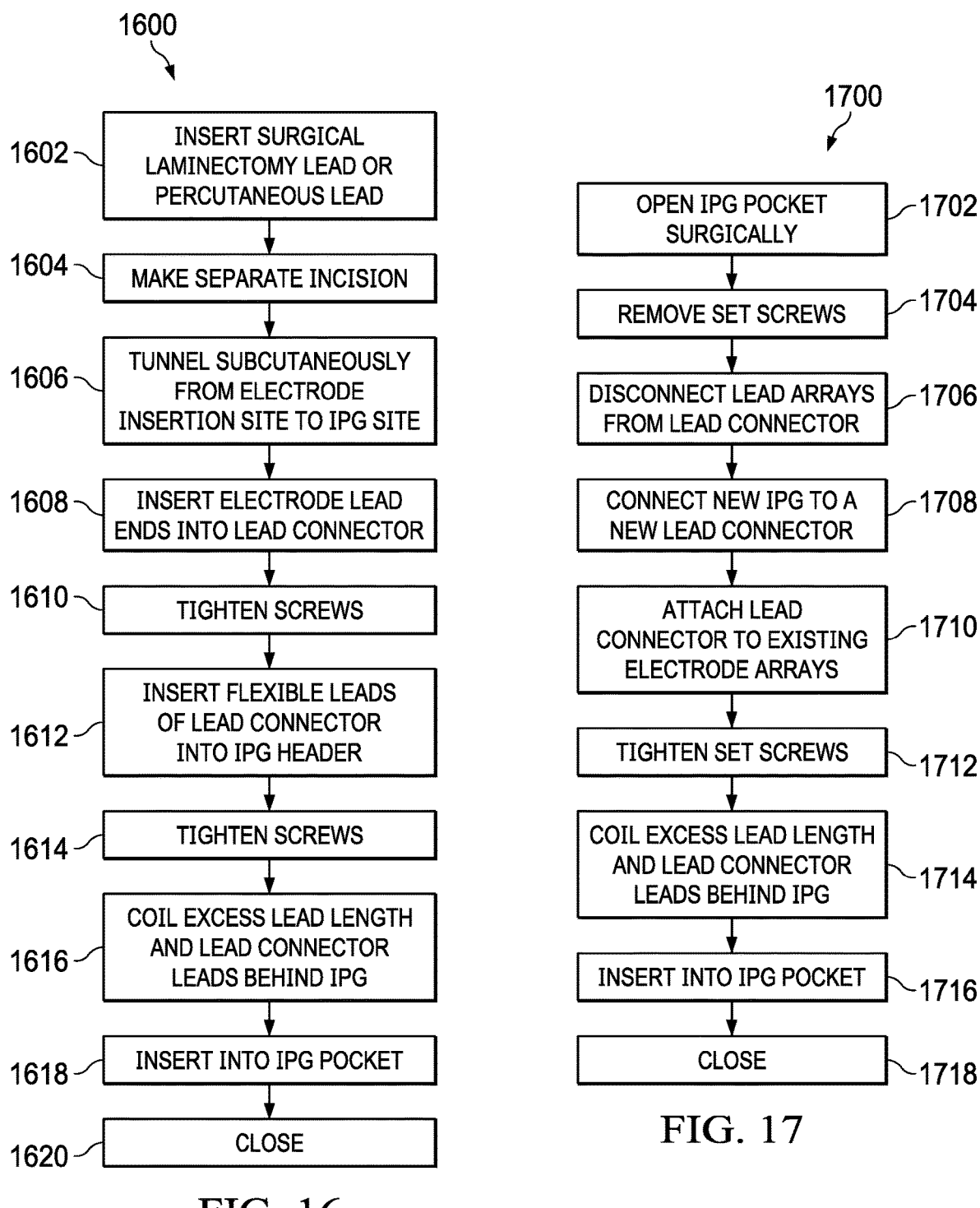

1600

1602 — INSERT SURGICAL LAMINECTOMY LEAD OR PERCUTANEOUS LEAD

1604 — MAKE SEPARATE INCISION

1606 — TUNNEL SUBCUTANEOUSLY FROM ELECTRODE INSERTION SITE TO IPG SITE

1608 — INSERT ELECTRODE LEAD ENDS INTO LEAD CONNECTOR

1610 — TIGHTEN SCREWS

1612 — INSERT FLEXIBLE LEADS OF LEAD CONNECTOR INTO IPG HEADER

1614 — TIGHTEN SCREWS

1616 — COIL EXCESS LEAD LENGTH AND LEAD CONNECTOR LEADS BEHIND IPG

1618 — INSERT INTO IPG POCKET

1620 — CLOSE

OPEN IPG POCKET SURGICALLY — 1702

REMOVE SET SCREWS — 1704

DISCONNECT LEAD ARRAYS FROM LEAD CONNECTOR — 1706

CONNECT NEW IPG TO A NEW LEAD CONNECTOR — 1708

ATTACH LEAD CONNECTOR TO EXISTING ELECTRODE ARRAYS — 1710

TIGHTEN SET SCREWS — 1712

COIL EXCESS LEAD LENGTH AND LEAD CONNECTOR LEADS BEHIND IPG — 1714

INSERT INTO IPG POCKET — 1716

CLOSE — 1718

FIG. 17

APPARATUS AND METHOD FOR INCORPORATION OF OPTICAL SENSING INTO NEUROSTIMULATION SYSTEMS

CROSS-REFERENCE TO RELATED APPLICATIONS

This application is a continuation-in-part of U.S. application Ser. No. 15/879,415, filed on Jan. 24, 2018, now U.S. Pat. No. 11,185,706, granted on Nov. 30, 2021, which claims priority benefit from to U.S. Provisional Patent Application No. 62/449,933, filed Jan. 24, 2017. Each patent application identified above is incorporated here by reference in its entirety to provide continuity of disclosure.

FIELD OF THE INVENTION

This disclosure relates generally to spinal cord stimulation (SCS) and technique for automatic adjustments of SCS using reflectometry.

BACKGROUND OF THE INVENTION

Chronic pain may arise from a variety of conditions, most notably from nerve injury as in the case of neuropathic pain, or from chronic stimulation of mechanical nociceptors such as with spinal pain. Functional ability may be severely impacted by pain, which often is refractory to pharmacological and surgical treatment. In such cases, spinal cord stimulation ("SCS") can be an effective treatment for pain by modulating physiological transmission of pain signals from the periphery to the brain. This may be achieved by applying electrical impulses to the spinal cord via an electrode array placed in the dorsal epidural space.

In FIG. 1, spinal column 100 is shown to have a number of vertebrae, categorized into four sections or types: lumbar vertebrae 102, thoracic vertebrae 104, cervical vertebrae 106 and sacral vertebrae 108. Cervical vertebrae 106 include the 1st cervical vertebra (C1) through the 7th cervical vertebra (C7). Just below the 7th cervical vertebra is the first of twelve thoracic vertebrae 104 including the 1st thoracic vertebra (T1) through the 12th thoracic vertebra (T12). Just below the 12th thoracic vertebrae 104, are five lumbar vertebrae 102 including the 1st lumbar vertebra (L1) through the 5th lumbar vertebra (L5), the 5th lumbar vertebra being attached to sacral vertebrae 108 (S1 to S5), sacral vertebrae 108 being naturally fused together in the adult. Electrical lead 110 is implanted between thoracic vertebrae 104, such that electrical lead 110 may deliver an electric current to spinal root nerves. Electrical lead 110 is attached via lead wire 112 to implantable pulse generator ("IPG") 116. IPG 116 has a header 114 that allows lead wire 112 to attach, but can be removed to allow IPG 116 to be replaced or serviced without disturbing electrical lead 110.

Referring to FIG. 2, alternate electrical leads 200 are shown. Percutaneous lead 202 includes optical fiber 204, optical element 206, electrodes 208 and contacts 210. Optical fiber 204 is coupled to optical element 206. Percutaneous lead 202 also includes electrical wires. Percutaneous lead 214 is of similar construction having optical element 218, electrodes 220, contacts 222, and optical fiber 216. The optical fibers are used to transmit light signals to be used for position detection of the spinal cord, as known in the art.

Referring to FIG. 3, a cross-sectional view of vertebra 300 is shown enclosing spinal cord 302. Percutaneous lead 304 and percutaneous lead 306 are implanted in epidural space 308 of vertebra 300 between dura 310 and the walls of the spinal canal 312. In a preferred embodiment, the percutaneous leads are implanted side-by-side at a predetermined distance apart, adjacent, and generally parallel to, each other. Placement of percutaneous leads 304 and 306 can be accomplished through insertion of the leads through needles placed percutaneously into the epidural space.

Referring to FIG. 4A, a surgical lead is shown. Surgical lead 400 includes an elastomeric housing 401 connected to lead 410 and to lead 411. Embedded in elastomeric housing 401, are optical fiber 402, optical fiber 403, electrodes 412 and electrodes 413. Optical fiber 402 is terminated with optical element 408. Optical fiber 403 is terminated with optical element 409. Lead 410 encloses optical fiber 402 and wires 404 which are terminated in opto-electrical connector 406. Lead 411 encloses optical fiber 403 and wires 405 which are terminated in opto-electrical connector 407. The fibers are used to accommodate reflectometry.

Referring to FIG. 4B, thoracic vertebra 450 is shown. The thick oval segment of bone forming the anterior aspect of vertebra 450 is vertebral body 452. Vertebral body 452 is attached to bony vertebral arch 454 through which spinal nerves 456 run. Vertebral arch 454, forming the posterior of vertebra 450, is comprised of two pedicles 458, which are short stout processes that extend from the sides of vertebral body 452 and bilateral laminae 460. The broad flat plates that project from pedicles 458 join in a triangle to form a hollow archway, spinal canal 462. Spinous process 464 protrudes from the junction of bilateral laminae 460. Transverse processes 466 project from the junction of pedicles 458 and bilateral laminae 460. The structures of the vertebral arch protect spinal cord 468 and spinal nerves 456 that run through the spinal canal.

Surrounding spinal cord 468 is dura 470 that contains cerebrospinal fluid (CSF) 472. Epidural space 474 is the space within the spinal canal lying outside the dura.

An IPG delivers pulses of electrical current to the electrode array, which stimulates targeted neurons within the ascending tracts of the spinal cord and disrupts the perception of pain. Controlling the amplitude of the stimulating electrical current is paramount to success of spinal cord stimulation. Applying inadequate current will fail to depolarize the targeted neurons, rendering the treatment ineffective. Conversely, application of too strong a current will depolarize the targeted neurons, but also stimulate additional cell populations which renders the perception of a noxious stimulation.

Establishing a consistent, therapeutic, and non-noxious level of stimulation is predicated upon establishing an ideal current density within the spinal cord's targeted neurons. Fundamentally, this should be a simple matter of establishing an optimal electrode current given the local bulk conductivity of the surrounding tissues. Unfortunately, in practice, the optimal electrode current changes as a function of patient position and activity due to motion of the spinal cord as the spinal cord floats in cerebrospinal fluid within the spinal canal. Significant changes in distance between the epidural electrode array and the targeted spinal cord neurons have been shown to occur. Consequently, it is preferred to dynamically adjust the electrode stimulating current as a function of distance between the electrode array and the spinal cord.

Dynamic modulation of spinal cord stimulator electrode current as a function of distance between the electrode array and the spinal cord thus has several benefits. Too high a stimulation current can be avoided, thus reducing the prospects of noxious stimulation and potentially reducing device power consumption. Too low a stimulation current can be avoided, thus eliminating periods of inadequate stimulation and compromised therapeutic efficacy.

A patient who is a candidate for treatment first undergoes a trial period whereby electrical leads are implanted percutaneously. The leads are connected to an IPG that is worn outside the body. Percutaneous leads connected to an external pulse generator provide certain advantages that make them useful for trial periods, because they can be installed without the need for major surgery. However, having the leads connected to an external IPG presents risks from potential injury or infection. Hence, for patients requiring long-term treatment, the IPG is connected to the leads subcutaneously and permanently implanted.

The IPG is typically implanted near the upper buttocks or flank. The IPG is intended to remain in a single orientation after implantation, and therefore must be fitted into a pocket of tissue that is no larger than necessary. Both the incision and pocket created must therefore match dimensions of the IPG used. An improper fit risks movement of the IPG, which could impede charging or tangle the electrode leads.

One challenge to IPG treatment is that the percutaneous leads are susceptible to movement over time. As the leads move, the distance to the spinal cord segment changes, requiring a new level of electrical current to maintain the efficacy of treatment. One way of addressing this challenge is through the use of reflectometry. An optical signal can be transmitted into the surrounding tissue, and collected by a sensor to calculate the approximate distance between the electrode and the target nerve. An example of this technology is shown in U.S. Pat. No. 10,035,019 to Wolf.

Another challenge to IPG treatment is the long-term survival of the electrode array and optoelectronics in the harsh in vivo environment. Functional and mechanical degradation may occur with the ingress of body fluids. Proteins common in the blood and interstitial fluid are known to bind to metallic ions, leading to corrosion. Some materials can trigger an immune response and potentially a change in the local pH balance of the implantation site. Specialized polymers and epoxies can avoid some of these problems, but often exhibit unacceptably high levels of cytotoxicity. Moreover, electronic devices implanted in the body must be sealed, because bodily fluids contain a great number of ions, such as sodium ions, that are not electrically inert.

Hermetic sealing of electronics is generally required for long-term sustainability. Current manufacturing techniques generally utilize potting of electronics within a biocompatible epoxy. Epoxies are desirable materials to achieve biocompatibility, but do not provide a lasting hermetic seal. Epoxies can leak, allowing bodily fluids to penetrate into the implant, at a rate of between $10^{-5}$ and $10^{-6}$ cubic centimeters of fluid per second. At such a rate, epoxy-coated implants will typically have a viability of no more than 15-20 years after implantation. Proper potting can achieve reliability upward of ten years, which is commensurate with the expected IPG battery life but falls short of the service life of an electrode array.

Another challenge to implementation of reflectometry for adaptive spinal cord stimulation has been the requirement to change the IPG to incorporate the necessary optoelectronic devices. Such a change would require a significant engineering endeavor, increased tooling and manufacturing costs, and overcoming considerable regulatory hurdles.

Another challenge of implementation of reflectometry is the need for repeated surgery. Components that must be very near the spinal cord, such as subcutaneous leads or optical sensors, are difficult to access after implantation, and should not be designed to require regular adjustment or maintenance because such would require repeated spinal surgery. The number and risk level of the later surgeries required to maintain the IPG systems should be minimized. Currently, batteries in IPGs must be replaced approximately once every 3-7 years. However, optoelectronics are anticipated to require replacement approximately once every 7-10 years. Doing so typically requires surgery on the spine itself, as the optics must be placed near the targeted spinal cord segment. The entire system must be replaced every 15-20 years.

The prior art has attempted to address these challenges in a number of ways.

For example, U.S. Pat. No. 6,011,993 to Tzviskos, et al. describes a method of making a strong ceramic case that can house electronics with a good hermetic seal for implantation into the body. However, the patent does not describe how to effectively connect electrical leads or optical fibers, nor does it describe a system for replacing a failing battery.

U.S. Pat. No. 6,324,428 to Weinberg, et al. describes a design for a medical implant that contains the internal electronics in a preferred configuration that minimizes the volume of the implant, making it easier to implant. However, the patent does not describe any designs that could alleviate the need for, or degree of risk involved in, follow up surgeries after implantation.

Similarly, U.S. Pat. No. 7,742,817 to Malinowski, et al. describes an IPG with connectors for electrical leads and an epoxy coating for biocompatibility. However, the patent does not disclose the use of optics in the design to achieve proper pulse strength.

Thus, there is a need in the art for a connector which attaches to an existing IPG without significant reengineering. There is also a need for placement of optoelectronics in a position to minimize the effects of biodegradation and repeated high-risk surgery.

SUMMARY OF THE INVENTION

To achieve the requirements for indefinite lifetime of the electrode array and requiring no physical changes to the IPG, while allowing for IPG battery changes at up to 10 year intervals, the optoelectronics may be housed in a hermetically-sealed connector which is easily accessed and changed at the time of IPG replacement. The connector acts as an interface between the leads that connect to the electrode array and the IPG. The connector consists, generally, of a body having ports which accommodate electrode leads, and flexible leads which accommodate the IPG header. The electrode leads incorporate optical fiber assemblies which convey light either to or from the lead tip to the optoelectronics which are housed in the connector. The leads are inserted into the connector. The connector is then connected to the IPG header. Two electrode contacts from each of two leads are repurposed to serve the optoelectronics in the connector. The connector leads are kept short so that the connector may be "tucked" behind the IPG during implantation so that it may be changed easily when the IPG is replaced. Existing IPGs generally have 16, 24, or 32 channels of which four or fewer would be repurposed for operation of the optoelectronics. Placement of the optoelectronics in the connector assures that the optoelectronics will be replaced at intervals less than the anticipated lifetime of the hermetic potting.

BRIEF DESCRIPTION OF THE DRAWINGS

The following disclosure is understood best in association with the accompanying figures. Like components share like numbers.

FIG. 12 is a schematic of a preferred embodiment of the laminectomy lead connector optoelectronics.

FIG. 13A is state chart of a preferred embodiment of a firmware program the processor.

FIG. 13B is a state chart of a preferred embodiment of a firmware program of the processor.

FIG. 15 is a preferred embodiment of a look-up table for light intensity versus electrode voltage and wave form.

FIG. 16 is a flowchart of a preferred method of installing a lead connector of a preferred embodiment.

FIG. 17 is a flowchart of a preferred method of securing an IPG.

DETAILED DESCRIPTION OF THE INVENTION

Figure 1:
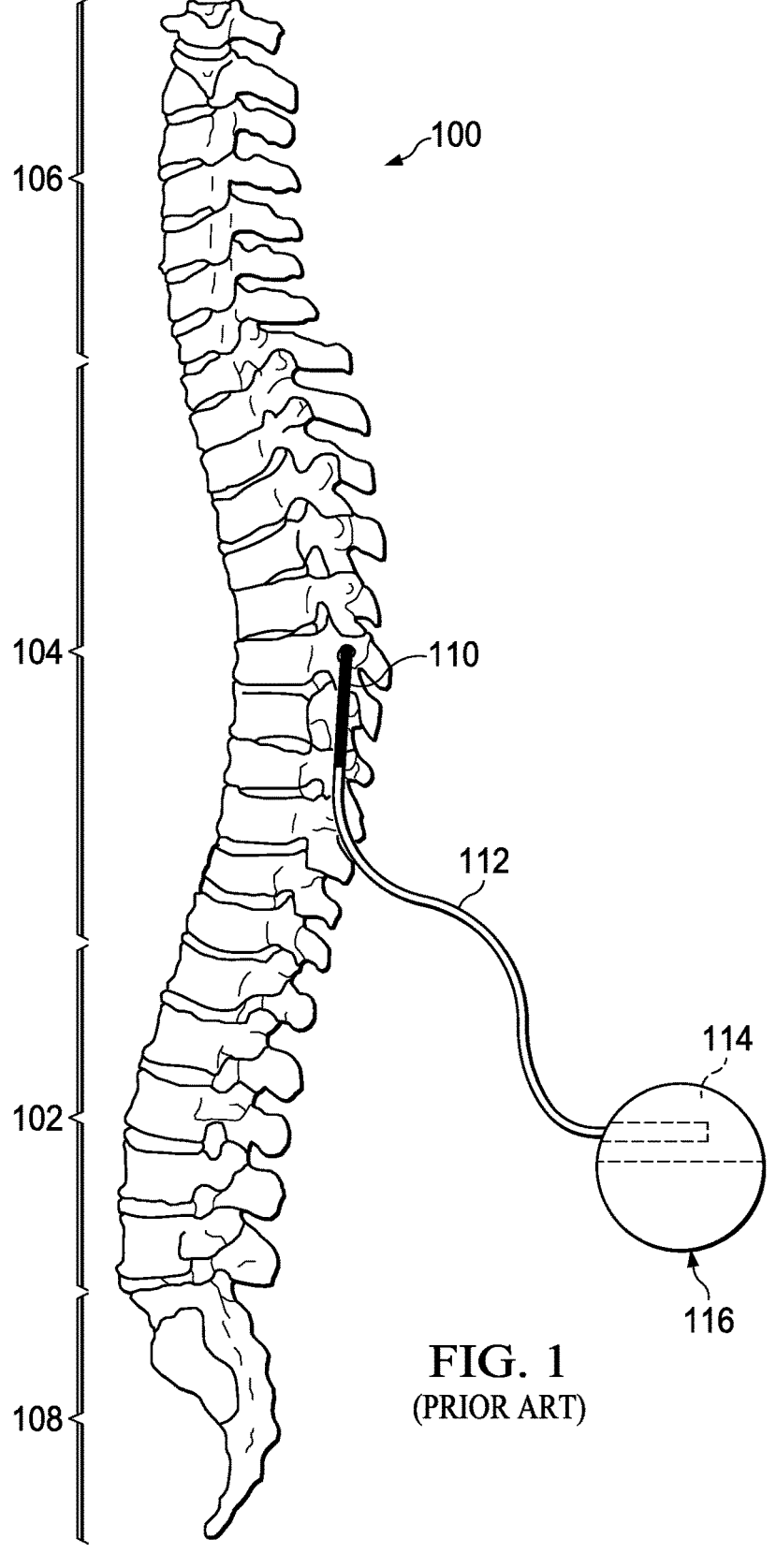
FIG. 1 shows a view of the human spine showing the various types of vertebrae and an approximate position of an electrode array for spinal cord stimulation.
Figure 2:
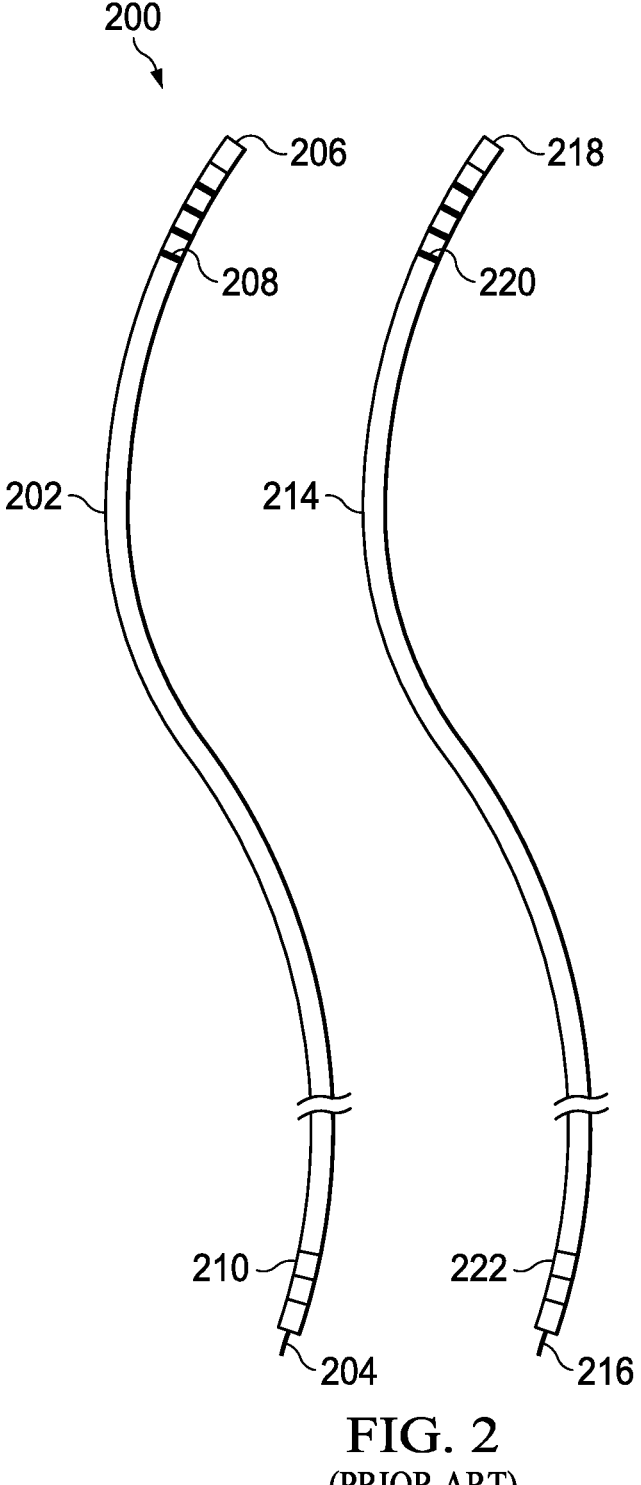
FIG. 2 shows a perspective view of a preferred embodiment of a paired percutaneous lead.
Figure 3:
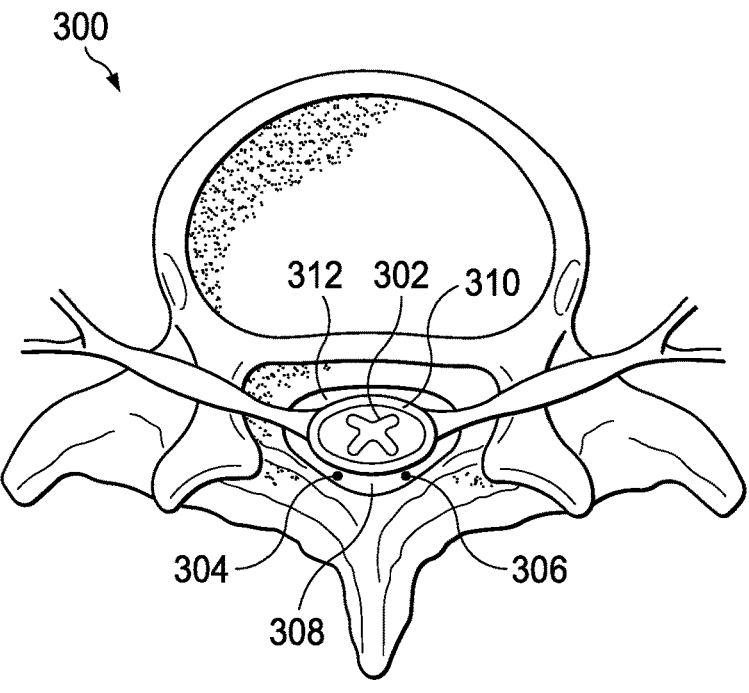
FIG. 3 shows preferred placement of a paired percutaneous surgical lead in a spinal column.
Figure 4B:
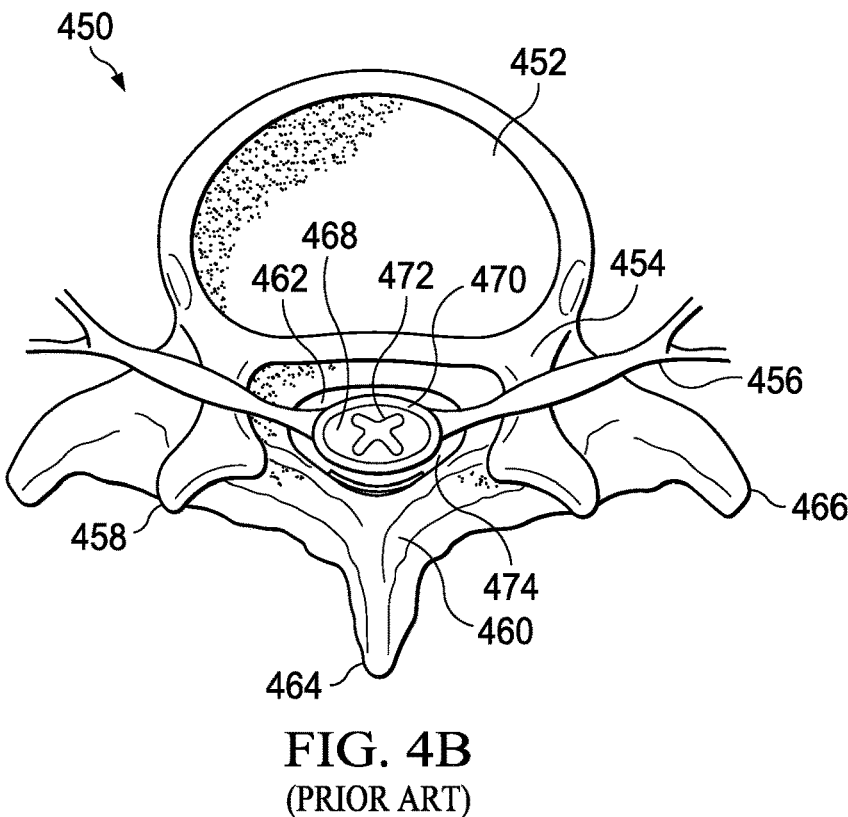
FIG. 4B shows an axial view of a thoracic vertebra indicating the position of the spinal cord and an electrode array for spinal cord stimulation.
Figure 4A:
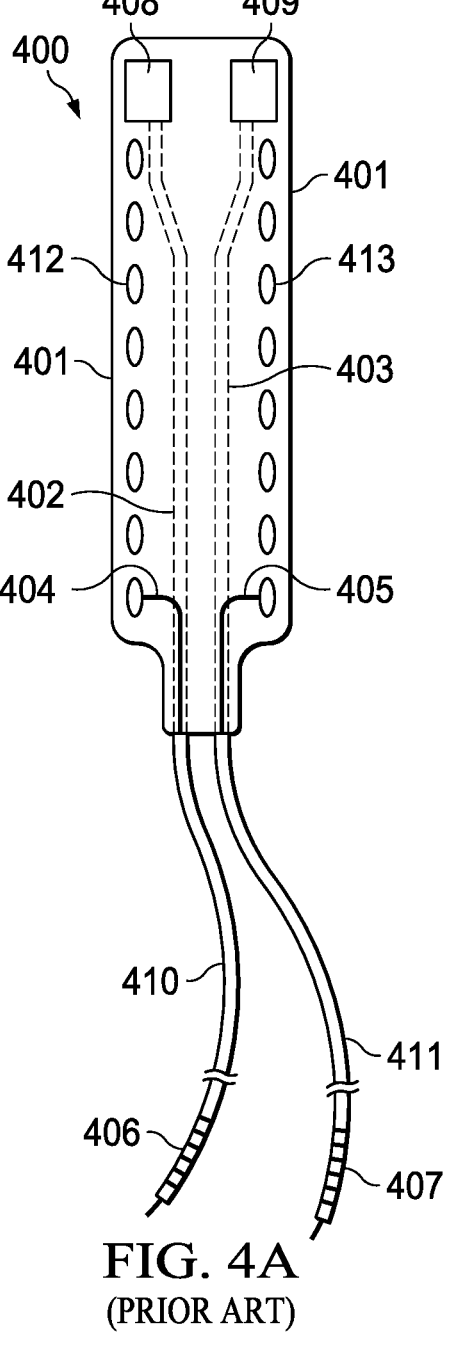
FIG. 4A shows a preferred embodiment of a surgical lead.
Figure 5:
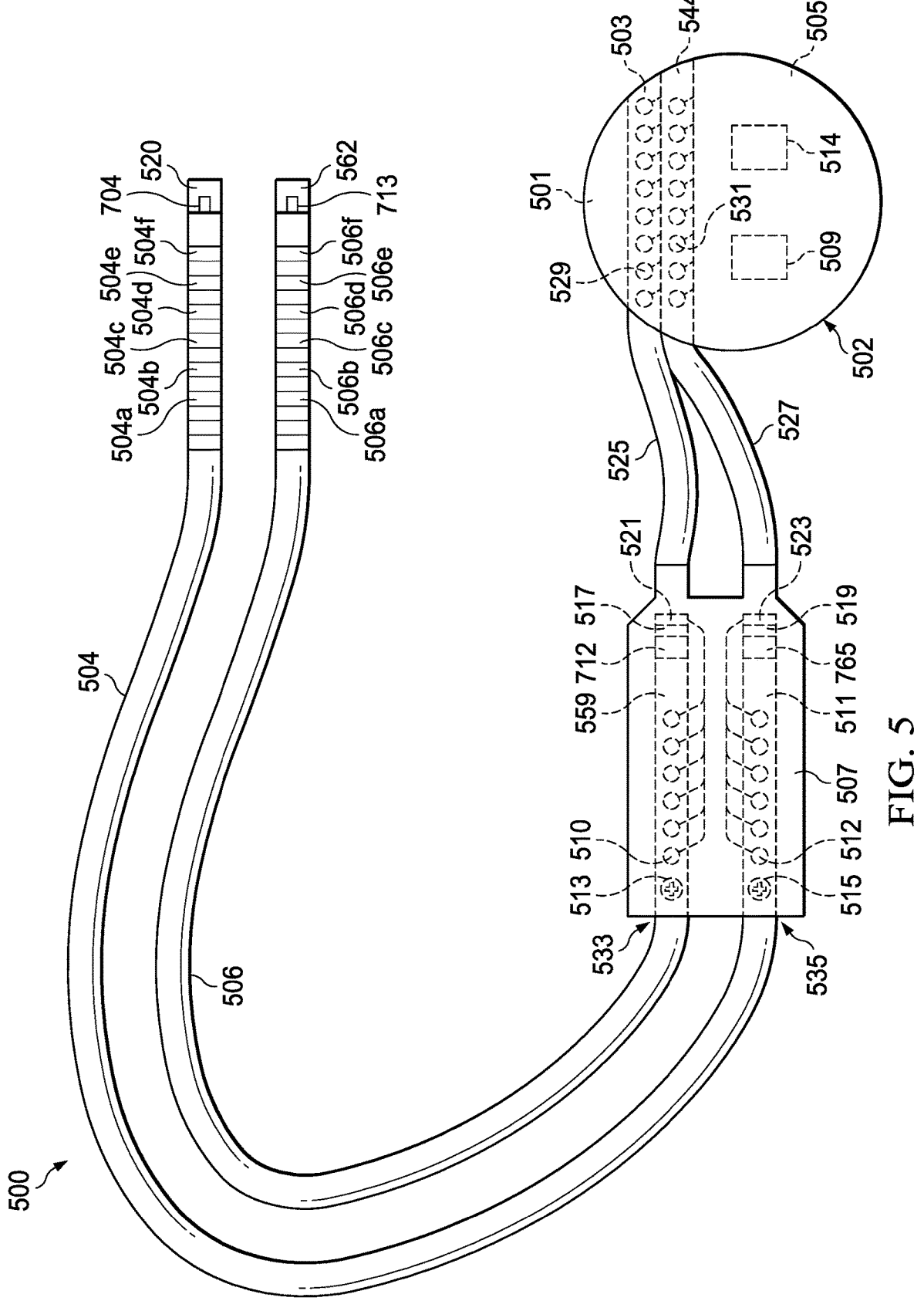
FIG. 5 is a system drawing of a preferred embodiment of the percutaneous lead connector system.

Turning then to FIG. 5, percutaneous connector system 500 includes IPG 502 connected to percutaneous lead connector 507 by flexible leads 525 and 527. Percutaneous lead connector 507 is in turn connected to flexible leads 504 and 506.

IPG 502 further includes IPG body 505. In a preferred embodiment, IPG body 505 is a stainless steel container capable of being hermetically sealed. IPG body 505 houses battery 509 operatively connected to processor 514. The processor is preferably a MSP430 microprocessor available from Texas Instruments. IPG 502 further includes connector arrays 503 and 544 included in header 501. In a preferred embodiment, header 501 is hermetically sealed to IPG body 505. In a preferred embodiment, IPG 502 is a commercially available spinal cord stimulator generator (IPG). Connector array 503 includes contacts 529. Connector array 544 includes contacts 531. In this embodiment, the IPG provides eight contacts in each connector array. Two of the connectors in each array are used to transmit control voltages to and from LEDs and optical sensors, as will be further described.

Percutaneous lead connector 507 includes connector array 559 and connector array 511. In a preferred embodiment, the connector body can be formed of poly (methyl methacrylate), polyvinyl chloride, a flexible Silastic elastomer, or a suitable epoxy resin. Connector array 559 includes contacts 510. Connector array 511 includes contacts 512. As will be further described, contacts 510 are connected to contacts 529 through flexible lead 525. As will be further described, contacts 512 are connected to contacts 531 through flexible lead 527.

Percutaneous lead connector 507 further comprises cylindrical port 533 and cylindrical port 535. Cylindrical port 533 accommodates flexible lead 506. Cylindrical port 535 accommodates flexible lead 504. Flexible lead 504 includes electrodes 504a, 504b, 504c, 504d, 504e and 504f and transparent tip 520, as will be further described. Flexible lead 506 includes electrodes 506a, 506b, 506c, 506d, 506e and 506f and transparent tip 562, as will be further described. In a preferred embodiment, wires (not shown) are encapsulated in flexible lead 504 and individually connect electrodes 504a-504f to contacts 512. Likewise, wires (not shown) are encapsulated in flexible lead 506 and individually connect electrodes 506a-506f to contacts 510.

Cylindrical port 533 houses lens array 517 and LED 521, as will be further described. Likewise, cylindrical port 535 houses lens array 519 and light to frequency converter 523, as will be further described.

Transparent tip 520 is optically connected by an internal fiber optic cable, to lens array 519. Likewise, transparent tip 562 is optically connected by an internal fiber optic cable to lens array 517.

Figure 6A:
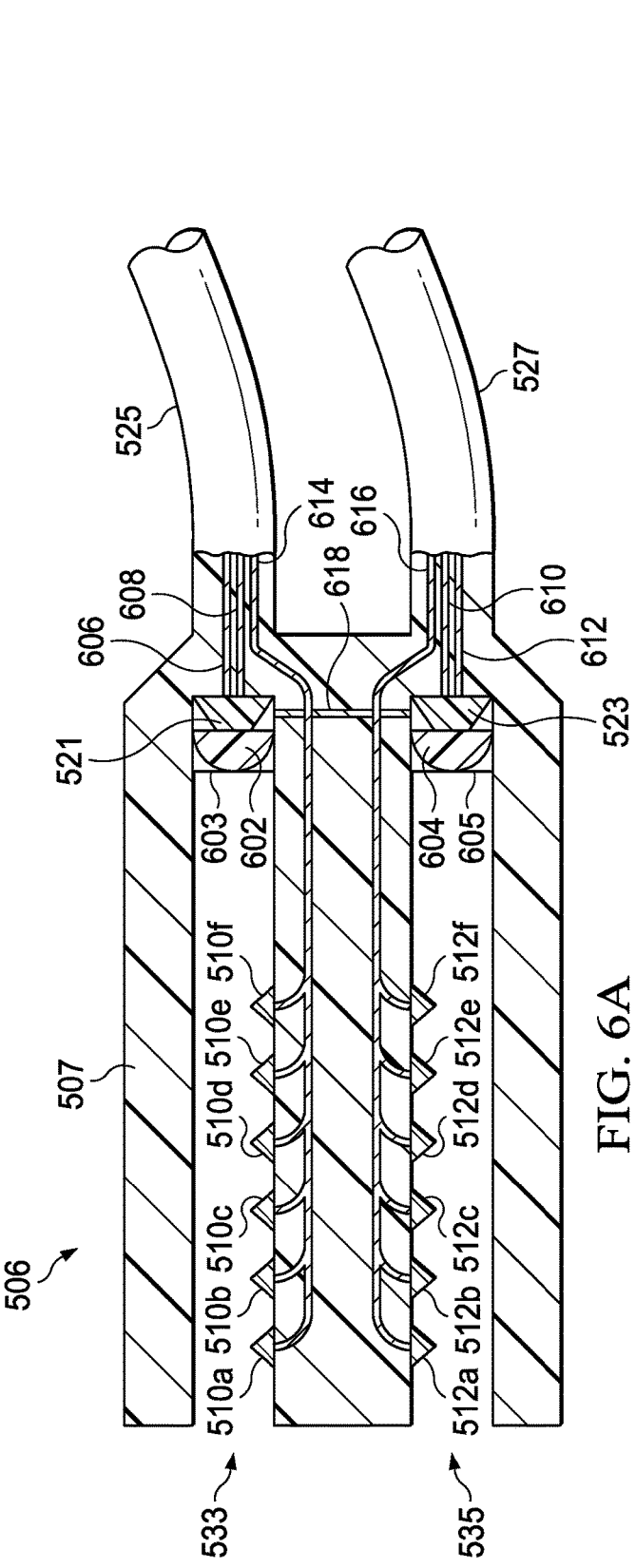
FIG. 6A is a cross sectional drawing of a preferred embodiment of the percutaneous lead connector.

Turning then to FIG. 6A, percutaneous lead connector 507 will be further described. Cylindrical port 533 is typically 1.5 millimeters in diameter (±10%). Similarly, cylindrical port 535 is typically 1.5 millimeters in diameter (±10%). Lens array 517 is rigidly fixed at the proximal end of cylindrical port 533 by a suitable epoxy. Lens array 517 further comprises coupling surface 603 and lens 602. In a preferred embodiment, lens 602 is encased in poly (methyl methacrylate). The encasement forms coupling surface 603, which is optically polished. In a similar way, lens array 519 is rigidly fixed at the proximal end of cylindrical port 535. Lens 604, in a preferred embodiment, is encased in poly (methyl methacrylate), which is optically polished to form coupling surface 605. Lens 602 and lens 604, in a preferred embodiment, are collimating lenses designed to reduce light loss. LED 521 is positioned adjacent lens 602 at the proximal end of cylindrical port 533. In a preferred embodiment, LED 521 is a high-speed, infrared emitting diode of about 850 nanometers wavelength. A preferred diode is available as part no. 1850VSMY available from Vishay Intertechnology, Inc. of Malvern, Pennsylvania. In other embodiments, light emitting diodes emitting light in the wavelength range of between about 600 and about 2500 nanometers may also be employed.

LFC 523 is positioned adjacent lens 604 and held in place by a suitable epoxy at the proximal end of cylindrical port 535. In a preferred embodiment LFC 523 is part no. TSL 238T high-sensitivity light to frequency converter available from Texas Advanced Optoelectronic Solutions of Plano, Texas. Using a digital detector obviates the requirements for analog-to-digital conversion which speeds processing time and conserves battery power. It also eliminates concerns over leakage currents affecting measurement accuracy, thereby increasing sustained accuracy and reducing calibration time and overhead. Flexible lead 525 includes eight wires which are, LED line 606, ground line 608, and electrode line bundle 614. Electrode line bundle 614 includes six individual wires. In a preferred embodiment, each of the wires in the electrode line bundles are comprised of a relatively inert nichrome. Flexible lead 527 includes eight wires, electrode line bundle 616, data line 610 and VCC line 612. Electrode line bundle 616 includes six individual wires. LED 521 is connected to LFC 523 by bridge connection 618, as will be further described. Bridge connection 618 supplies VCC and ground.

Figure 6B:
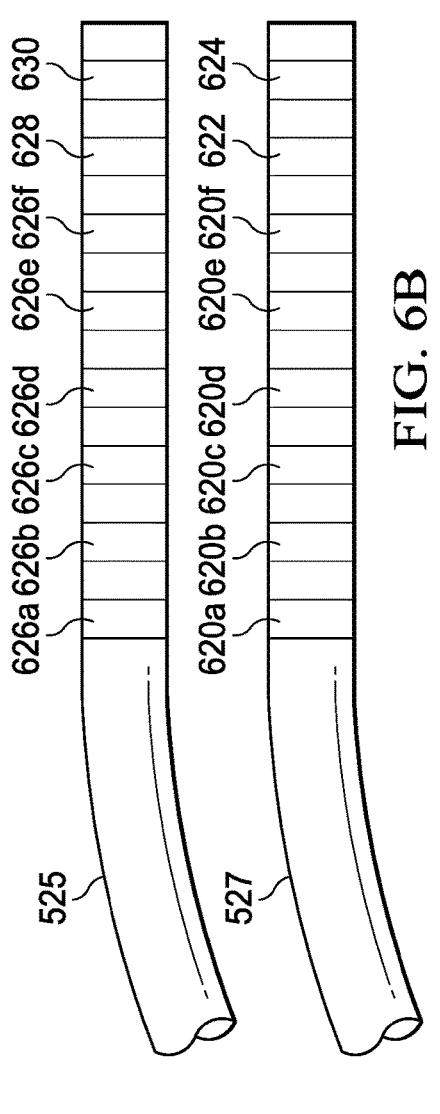
FIG. 6B is a preferred embodiment of the flexible leads of the percutaneous lead connector.

Turning then to FIG. 6B, flexible lead 525 includes electrodes 626a, 626b, 626c, 626d, 626e and 626f, 628 and 630. Each of electrodes 626a-626f is connected to a separate single wire in electrode line bundle 614. In a preferred embodiment, LED line 606 is connected to electrode 628. In a preferred embodiment, ground line 608 is connected to electrode 630. In this way, each of the electrodes is separately addressable.

Flexible lead 527 includes electrodes 620a, 620b, 620c, 620d, 620e and 620f, 622 and 624. In a preferred embodiment, data line 610 is connected to electrode 622. In a preferred embodiment, VCC line 612 is connected to electrode 624. Likewise, each of electrodes 620a-620f is connected to a separate single wire in electrode line bundle 616. In this way, each of the electrodes is separately addressable.

Cylindrical port 533 further includes integrally formed contacts 510a, 510b, 510c, 510d, 510e and 510f. Each of integrally formed contacts 510a-510f is individually connected to one wire in electrode line bundle 614. Cylindrical port 535 includes integrally formed contacts 512a, 512b, 512c, 512d, 512e and 512f. Each of integrally formed contacts 512a-512f is connected to an individual wire in electrode line bundle 616. In a preferred embodiment, each of integrally formed contacts 510a-510f and 512a-512f are conically formed and embedded in an interior surface of cylindrical ports 533 and 535, respectively. In a preferred embodiment, each of the integrally formed contacts is a raised conical shape, formed of a gold or a platinum alloy.

Figure 7A:
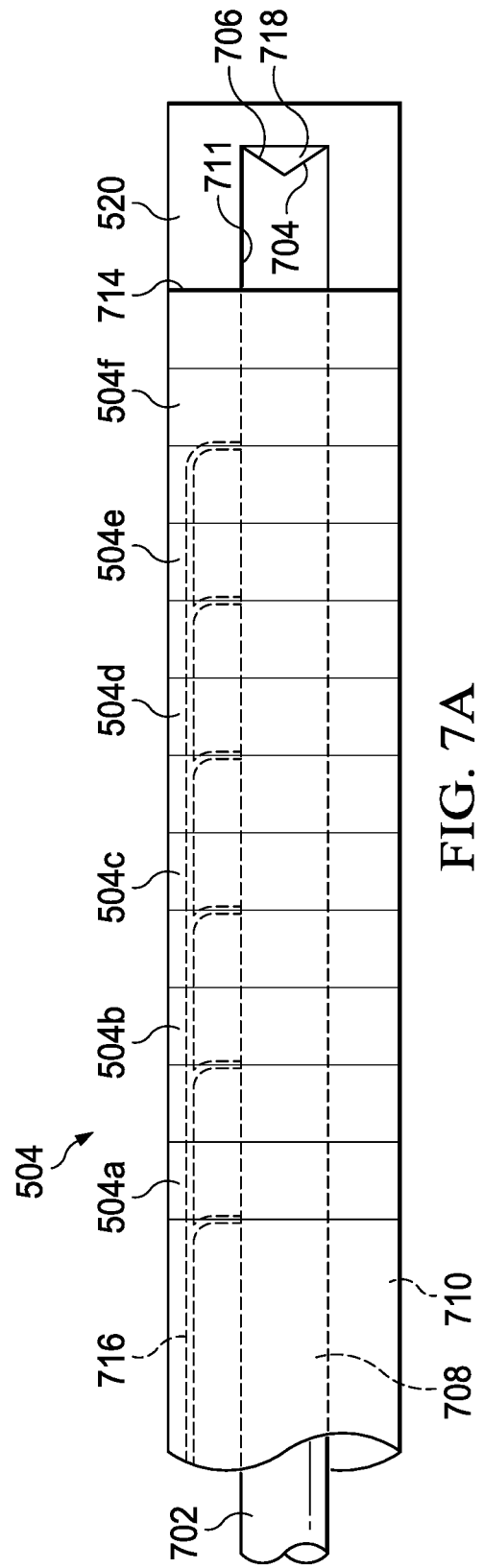
FIGS. 7A and 7B are drawings of a preferred embodiment of a flexible lead of the percutaneous lead connector.
Figure 7B:
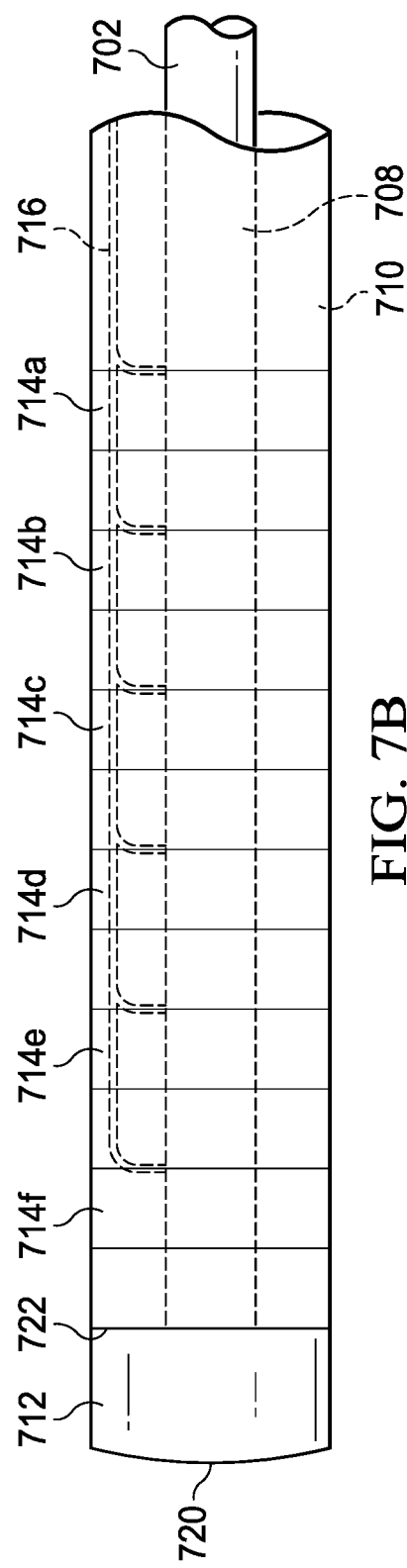

Moving then to FIGS. 7A and 7B, flexible lead 504 will be further described. Flexible lead 504 further comprises lead body 710. Lead body 710, in a preferred embodiment, is comprised of a biologically inert polymer such as pellathane-55D. The flexible lead is typically about 60 cm long and has a diameter of about 1.5 mm.

Cylindrical contacts 714a, 714b, 714c, 714d, 714e and 714f are embedded within lead body 710 at regular intervals. In a preferred embodiment, each of the electrodes is coaxial and comprised of platinum or platinum alloy and is positioned along the proximal end of flexible lead 504. The distal end of lead body 710 further comprises electrodes 504a-504f. Electrodes 504a-504f are cylindrical and coaxial, and in a preferred embodiment, are comprised of a platinum or a platinum alloy. Electrodes 504a-504f are spaced at regular intervals on the exterior surface of the lead body and, when assembled with percutaneous lead connector 507, form an electrical contact with each of integrally formed contacts 512a-512f. In a preferred embodiment, electrode 504a, is connected to integrally formed contact 512a. In a preferred embodiment, electrode 504b, is connected to integrally formed contact 512b. In a preferred embodiment, electrode 504c, is connected to integrally formed contact 512c. In a preferred embodiment, electrode 504d, is connected to integrally formed contact 512d. In a preferred embodiment, electrode 504e, is connected to integrally formed contact 512e. In a preferred embodiment, electrode 504f, is connected to integrally formed contact 512f.

In a preferred embodiment, electrode 504a is connected to an individual wire in electrode line bundle 716, which is, in turn, connected to cylindrical contact 714a. Electrode 504b is connected to an individual wire in electrode line bundle 716, which is, in turn, connected to cylindrical contact 714b. Electrode 504c is connected to an individual wire in electrode line bundle 716, which is, in turn, connected to cylindrical contact 714c. Electrode 504d is connected to an individual wire in electrode line bundle 716, which is, in turn, connected to cylindrical contact 714d. Electrode 504e is connected to an individual wire in electrode line bundle 716, which is, in turn, connected to cylindrical contact 714e. Electrode 504f is connected to an individual wire in electrode line bundle 716, which is, in turn, connected to cylindrical contact 714f.

Electrode line bundle 716 is formed integrally with lead body 710 and is isolated from contact with bodily fluids. Transparent tip 520 is located at the distal end of flexible lead 504. Transparent tip 520 is cylindrical and is attached to lead body 710 at interface 714 with a suitable epoxy adhesive. In a preferred embodiment, transparent tip 520 is comprised of poly (methyl methacrylate) and is optically transparent. Transparent tip 520 includes optical cavity 711. In a preferred embodiment, optical cavity 711 is cylindrical and is of an appropriate diameter to accommodate optical fiber assembly 702. In another preferred embodiment, the optical fiber assembly is allowed to float within the lead body. Binding of the optical fiber or the transparent tip to the lead body or electrodes is prevented by providing a gap at interface 714 of about 1/16".

Lead body 710 further comprises central lumen 708. The central lumen is typically used for positioning of the lead during surgery. However, after implantation the lumen is left open. Removably disposed within central lumen 708 is optical fiber assembly 702. The optical fiber composition is preferably a poly (methyl methacrylate), a biocompatible acrylic or a borosilicate glass. The cladding of the fiber is preferably a fluorinated polymer such as polytetrafluoroethylene or polyvinyl chloride. The optical fiber assembly may be inserted into the central lumen after implantation of the flexible lead or formed internally with the flexible lead at the time of manufacture. Optical fiber assembly 702 includes integrally formed collet 712 at its proximal end. Collet 712 is cylindrical and has a diameter approximately equal to that of lead body 710. Collet 712 includes polished optical surface 720. Polished optical surface includes a radius, which forms a collimating lens for efficient transfer of light. In a preferred embodiment, polished optical surface 720 is integrally formed with optical fiber assembly 702. In another preferred embodiment, collet 712 is separately machined from an optical glass and attached to optical fiber assembly 702 at interface 722. Optical fiber assembly 702 includes negative axicon 704 at its distal end. Negative axicon 704 includes a 45° inverted cone arrangement and produces a radial reflection perpendicular to the longitudinal axis of the lead.

Negative axicon 704 includes $TiO_2$ nanoparticle surface cladding 706 on its internal surface. Negative axicon 704 further includes backfill 718. In a preferred embodiment backfill 718 is comprised of a suitable epoxy, which binds the $TiO_2$ nanoparticle surface cladding to the interior surface of the negative axicon. Alternatively, the $TiO_2$ nanoparticles may be mixed into the backfill before application. In a preferred embodiment, the epoxy is Epotek 302. The $TiO_2$ nanoparticle surface cladding is important because it increases the amount of light reflected into or out of the optical fiber assembly.

Flexible lead 506 is of the same construction and has all similar components as flexible lead 504 and connects electrodes 506a-506f to integrally formed contacts 510a-510f, respectively, via an electrode line bundle, and physically positions collet 765 adjacent lens array 517. It also connects collet 765 to negative axicon 713 via a fiber optic lead internal to a central lumen in the lead. Negative axicon 713 is of similar structure to negative axicon 704. Flexible lead 506 is held in place by set screw 513. Flexible lead 504 is held in place by set screw 515.

Figure 8:
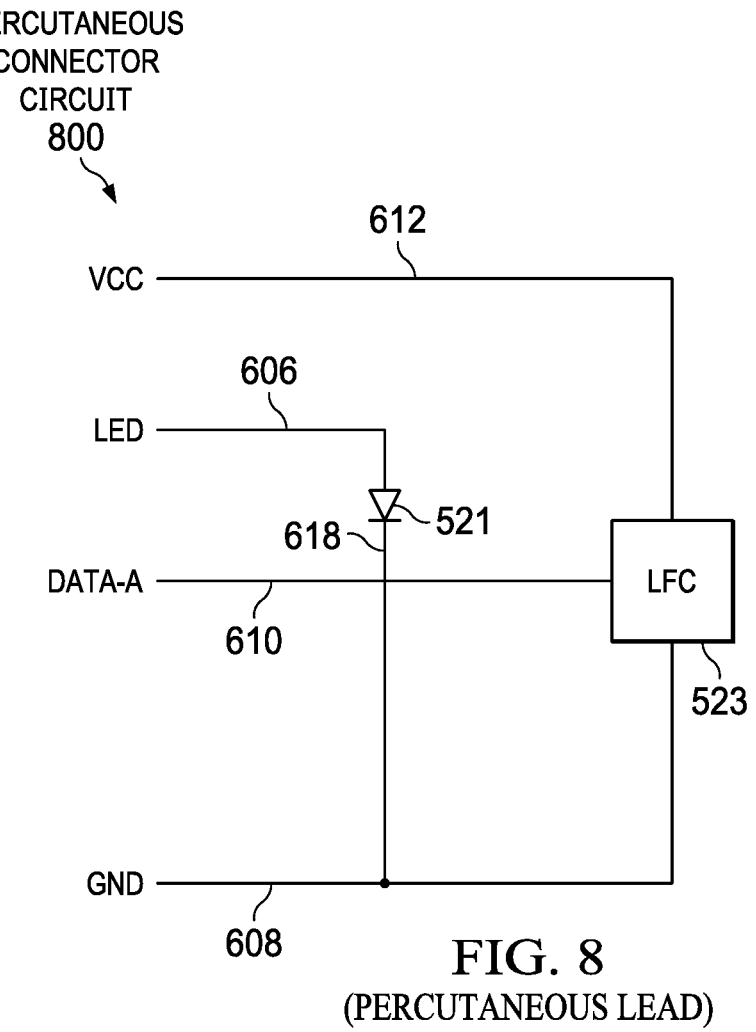
FIG. 8 is schematic of a preferred embodiment of a circuit of the percutaneous lead connector.

Referring to FIG. 8, percutaneous connector circuit 800 will be described. Percutaneous connector circuit 800 shows VCC line 612 connected to LFC 523. LFC 523 is also shown connected to data line 610 and ground line 608. LED 521 is shown connected to LED line 606 and bridge connection 618, which is also connected to ground line 608 and LFC 523.

Figure 9:
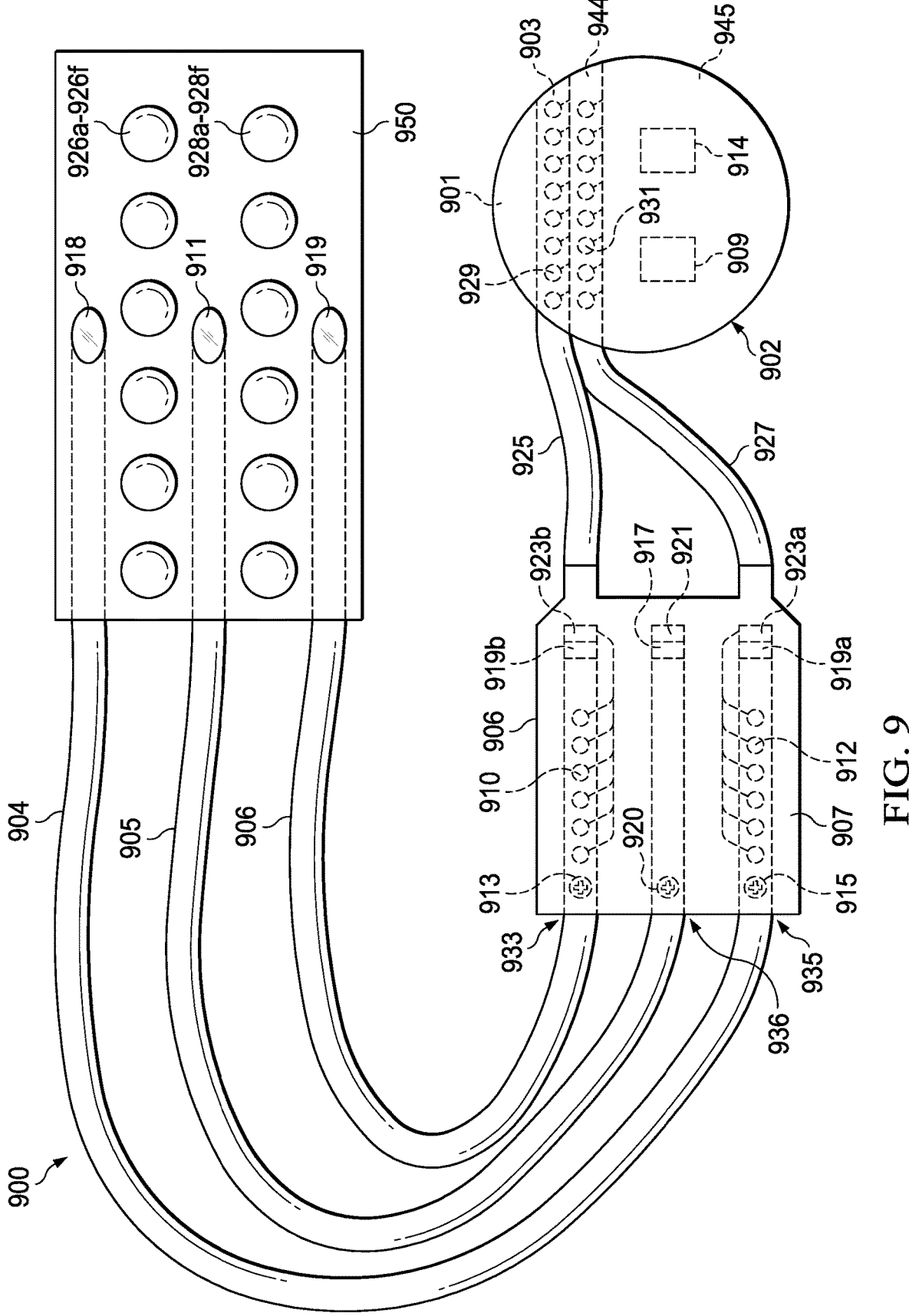
FIG. 9 is a system drawing of a preferred embodiment of a laminectomy lead connector system.

Turning then to FIG. 9, laminectomy lead connector system 900 will be described. Laminectomy lead connector system 900 is comprised of IPG 902 connected to laminectomy lead connector 916 which is in turn connected to paddle shaped laminectomy lead 950. IPG 902 is connected to laminectomy lead connector 916 by flexible lead 925 and flexible lead 927. Laminectomy lead connector 916 is connected to paddle shaped laminectomy lead 950 by flexible lead 904, flexible lead 905 and flexible lead 906.

IPG 902 comprises IPG body 945. IPG body 945 is hermetically sealed and includes battery 909 operatively connected to processor 914. In a preferred embodiment, processor 914 includes a MSP430 microprocessor core available from Texas Instruments of Dallas, Texas.

IPG 902 is connected to header 901. In a preferred embodiment, header 901 is hermetically sealed to IPG 902. Header 901 includes connector array 903 and connector array 944. In a preferred embodiment, each connector array includes eight contacts. Connector array 903 includes contacts 929. Connector array 944 includes contacts 931.

Laminectomy lead connector 916 includes connector body 907. In a preferred embodiment, connector body 907 is comprised of a flexible Silastic elastomer, polyvinyl chloride, poly (methyl methacrylate) or a suitable, biologically compatible epoxy. Connector body 907 is connected to IPG 902 through flexible lead 925 and flexible lead 927. Flexible lead 925 is connected to connector array 903. Flexible lead 927 is connected to connector array 944. Connector body 907 further comprises cylindrical port 933, cylindrical port 936 and cylindrical port 935. In a preferred embodiment, each of these cylindrical ports is approximately 1.5 millimeters in diameter (±10%).

Lens array 919a is rigidly positioned in the proximal end of cylindrical port 935, as will be further described. LFC 923a is rigidly connected to lens array 919a, as will be further described. Lens array 917 is rigidly positioned at the proximal end of cylindrical port 936. LED 921 is rigidly fixed to lens array 917, as will be further described. Lens array 919b is rigidly fixed at the proximal end of cylindrical port 933, as will be further described. LFC 923b is rigidly fixed to lens array 919b, as will be further described.

Connector body 907 supports six contacts 910 adjacent cylindrical port 933. Connector body 907 also supports six contacts 912 adjacent cylindrical port 935. Set screw 913 extends into cylindrical port 933 through a threaded hole (not shown). Set screw 920 extends into cylindrical port 936 through a threaded hole (not shown). Set screw 915 extends into cylindrical port 935 through a threaded hole (not shown). The number of contacts can vary depending on the number of electrodes.

Flexible lead 904 is integrally formed with paddle shaped laminectomy lead 950 and terminates in transparent window 918. Flexible lead 905 is integrally formed with paddle shaped laminectomy lead 950 and terminates in transparent window 911. Flexible lead 906 is integrally formed with paddle shaped laminectomy lead 950 and terminates in transparent window 919. Flexible lead 904 is connected to connector body 907 at cylindrical port 935 and held in place by set screw 915. Flexible lead 905 is connected to connector body 907 at cylindrical port 936 and is held in place by set screw 920. Flexible lead 906 is connected to connector body 907 at cylindrical port 933 and held in place by set screw 913. The number of flexible leads may vary. However, preferably there are three to provide for stereoscopic detection of the spinal cord position using reflectometry.

Figure 10A:
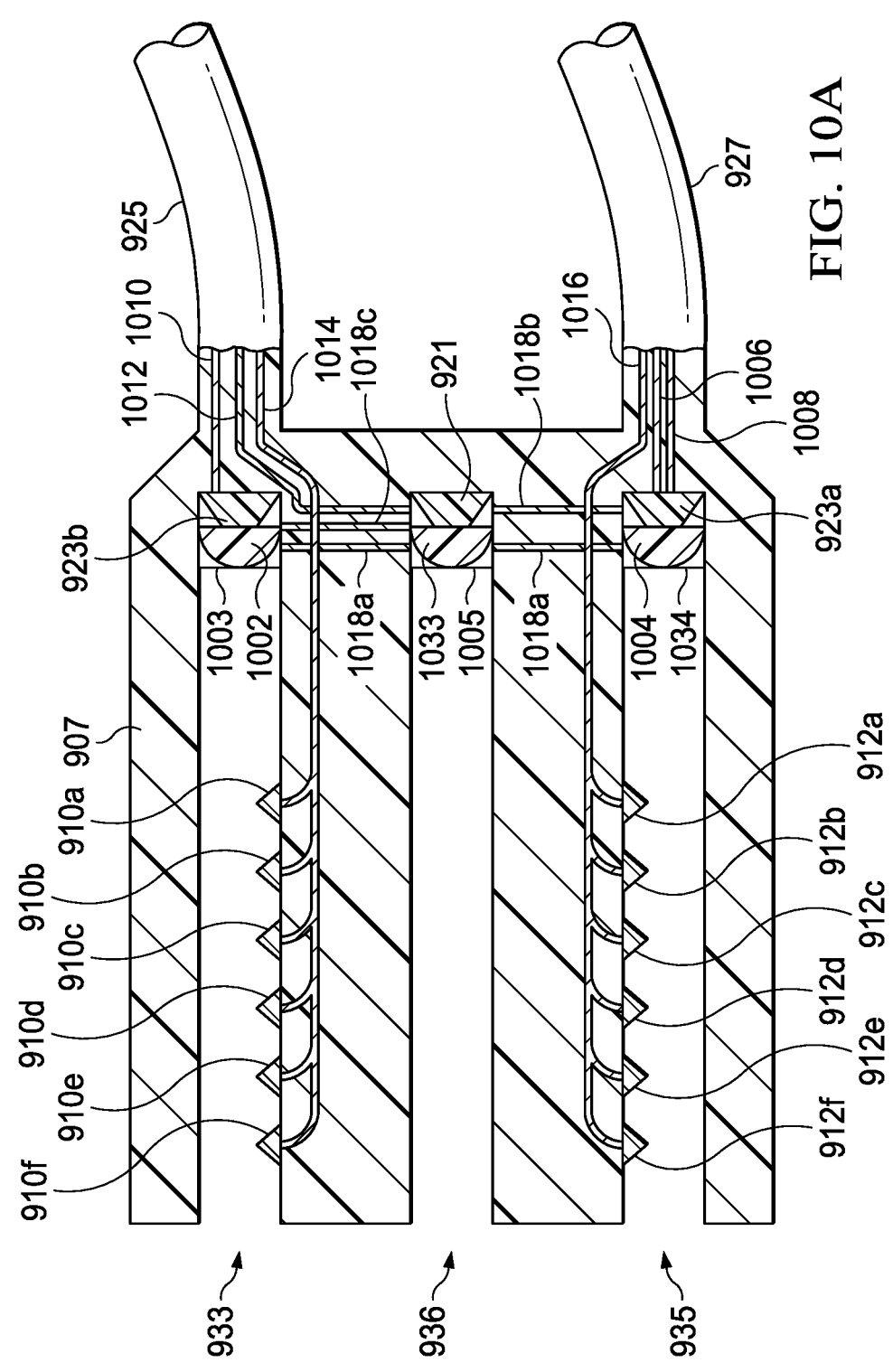
FIG. 10A is cross sectional drawing of a preferred embodiment of the laminectomy lead connector.
Figure 10B:
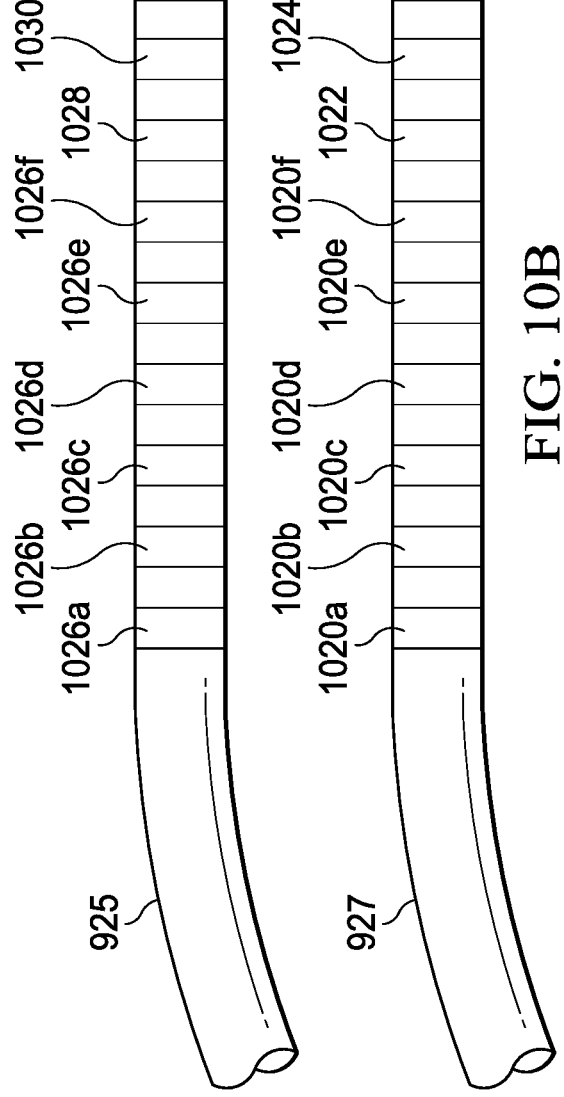
FIG. 10B is a drawing of the flexible leads of a preferred embodiment of a laminectomy lead contact.

Turning then to FIGS. 10A and 10B, connector body 907 includes integrally formed flexible lead 927 and integrally formed flexible lead 925. Integrally formed flexible lead 925 includes internal wire Data A line 1010, VCC line 1012 and electrode line bundle 1014. Electrode line bundle 1014 includes six separate wires. Data A line 1010 is connected to LFC 923b. VCC line 1012 is connected to LED 921. One wire each of electrode line bundle 1014 is connected to integrally formed contacts 910a, 910b, 910c, 910d, 910e and 910f. Integrally formed flexible lead 927 includes Data B line 1006, ground line 1008, and electrode line bundle 1016. Electrode line bundle 1016 includes six separate wires. One wire each of electrode line bundle 1016 is connected to integrally formed contact 912a, 912b, 912c, 912d, 912e and 912f. Data B line 1006 is connected to LFC 923a. Ground line 1008 is connected to LFC 923a. LFC 923a and LFC 923b are connected to LED 921 and VCC by bridge connection 1018b and bridge connection 1018c as will be further described. LFC 923a, LED 921 and LFC 923b are connected to ground by virtue of bridge connection 1018a, as will be further described.

Connector body 907 further comprises cylindrical port 933, cylindrical port 936 and cylindrical port 935. Each of integrally formed contacts 910a-910f is positioned adjacent cylindrical port 933 and comprises a conical metallic contact formed into the connector body. Each of integrally formed contacts 910a-910f is held in a fixed positioned by connector body 907. Integrally formed contacts 912a-912f are positioned adjacent cylindrical port 935. Each of integrally formed contacts 912a-912f is held in a fixed position by connector body 907. All of the integrally formed contacts, in a preferred embodiment, are shaped as conical metallic nodes made of a platinum or platinum alloy.

Lens array 919b includes lens 1002 adjacent coupling surface 1003. In a preferred embodiment lens 1002 is arranged to collimate light from collet 1112c. In a preferred embodiment lens 1002 is formed of an optical glass encased in poly (meth methacrylate) which forms coupling surface 1003 after polishing. Lens 1002 is held adjacent LFC 923b by a suitable epoxy. Similarly, lens array 917 further comprises lens 1033 and coupling surface 1005. In a preferred embodiment, lens 1033 is an optical glass and designed to collimate light from collet 1112b. Lens 1033, in a preferred embodiment, is encased in a poly (meth methacrylate) on which forms coupling surface 1005 after polishing In a preferred embodiment, lens 1033 is held adjacent LED 921 by a suitable epoxy. Similarly, lens array 919a is comprised of lens 1004 and coupling surface 1034. In a preferred embodiment, lens 1004 is an optical glass designed to collimate light from collet 1112*a*. Lens 1004 is encased in a poly (meth methacrylate) which forms a polished coupling surface 1034. In a preferred embodiment, lens 1004 is held adjacent LFC 923*a* by a suitable epoxy.

The proximal end of integrally formed flexible lead 925 includes cylindrical electrodes 1026*a*, 1026*b*, 1026*c*, 1026*d*, 1026*e* and 1026*f*, 1028 and 1030. One wire each of electrode line bundle 1014 is connected to one of cylindrical electrodes 1026*a*-1026*f*. In a preferred embodiment, cylindrical electrode 1028 is connected to Data A line 1010. In a preferred embodiment, cylindrical electrode 1030 is connected to VCC line 1012. Likewise, flexible lead 927 includes six cylindrical electrodes 1020*a*, 1020*b*, 1020*c*, 1020*d*, 1020*e* and 1020*f*, cylindrical electrode 1022 and cylindrical electrode 1024. One each of cylindrical electrodes 1020*a*-1020*f* is connected to one wire of electrode line bundle 1016. In a preferred embodiment, Data B line 1006 is connected cylindrical electrode 1022. In a preferred embodiment, ground line 1008 is connected to cylindrical electrode 1024. In this way, processor 914 can be programmed to access the VCC, data and ground lines by repurposing two each of contacts 931 and 929, which are typically used to transmit a stimulation voltage.

Figure 11A:
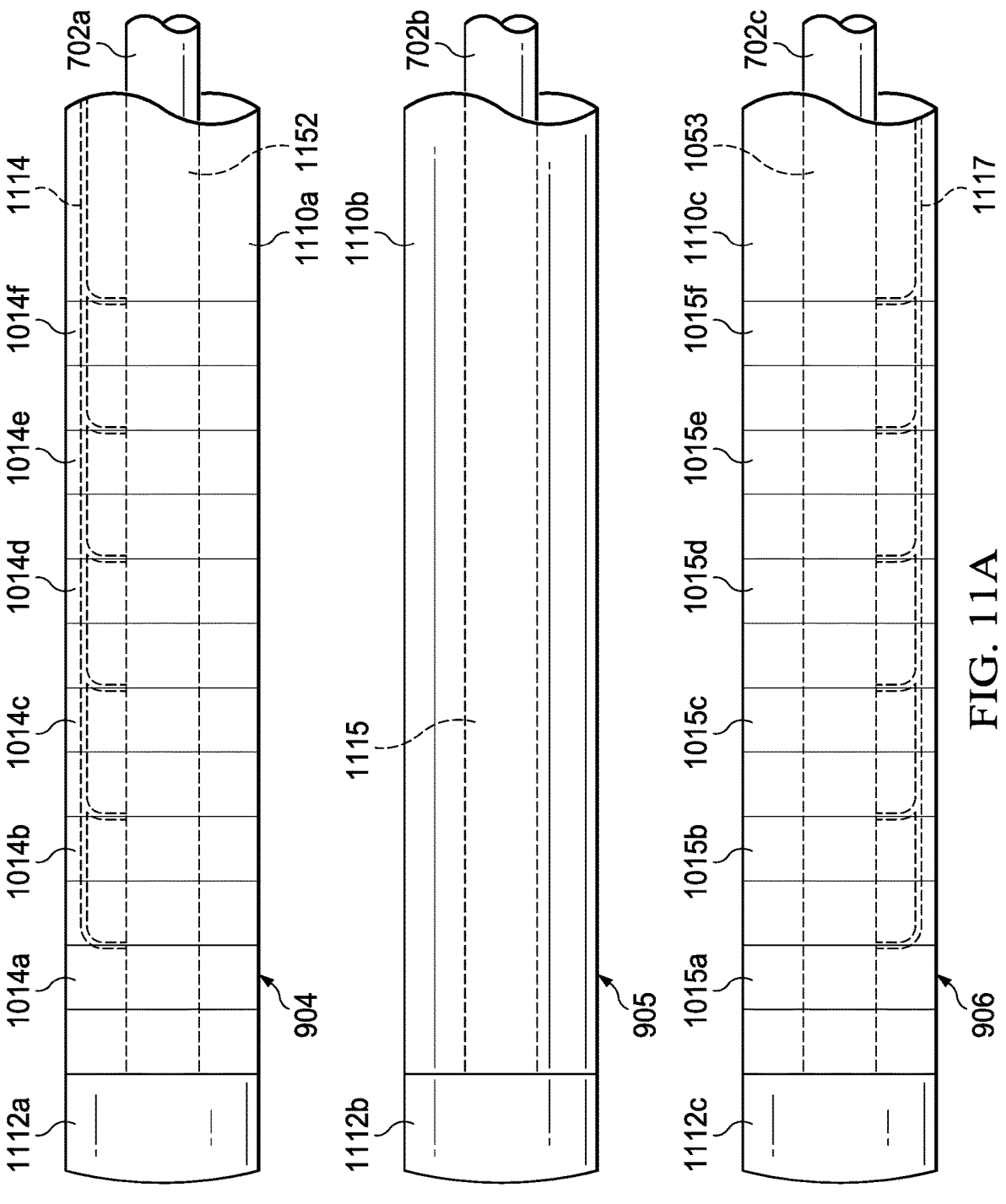
FIG. 11A is a cutaway drawing of a preferred embodiment of the flexible leads of a laminectomy lead contact.

Referring then to FIG. 11A, the proximal ends of flexible leads 904, 905 and 906 will be described. Flexible lead 904 comprises lead body 1110*a*. Lead body 1110*a* includes integrally formed electrode line bundle 1114 and optical fiber assembly 702*a*. Integrally formed electrode line bundle 1114 comprises six wires connected one wire each to cylindrical electrodes 1014*a*, 1014*b*, 1014*c*, 1014*d*, 1014*e* and 1014*f*. The number and positions of the wires is not critical and may vary depending on the number of electrodes required. The cylindrical electrodes are of similar composition and structure to those previously described.

Optical fiber assembly 702*a* comprises optical fiber 1152 integrally formed with collet 1112*a*. The structure of the fiber and the collet are similar to those previously described.

Flexible lead 905 further comprises lead body 1110*b* and integrally formed optical fiber assembly 702*b*. Optical fiber assembly 702*b* includes optical fiber 1115 integrally formed with collet 1112*b*. The structure and composition of the collet and the optical fiber are similar to those previously described.

Flexible lead 906 further comprises lead body 1110*c* and integrally formed optical fiber assembly 702*c*. Lead body 1110*c* further comprises cylindrical electrodes 1015*a*, 1015*b*, 1015*c*, 1015*d*, 1015*e* and 1015*f*. Lead body 1110*c* further comprises electrode line bundle 1117. In a preferred embodiment, electrode line bundle 1117 includes six individual wires, one each connected to cylindrical electrodes 1015*a*-1015*f*. Optical fiber assembly 702*c* further comprises optical fiber 1053 and collet 1112*c*. The structure and composition of the collet, the electrodes and the optical fiber are similar to those previously described.

When assembled, collet 1112*a* of flexible lead 904 is nested within cylindrical port 935 adjacent coupling surface 1034 and maintained there by set screw 915. Integrally formed contact 912*a* is held in contact with cylindrical electrode 1014*a*. Similarly, integrally formed contact 912*b* is held in contact with cylindrical electrode 1014*b*, integrally formed contact 912*c* is held in contact with cylindrical electrode 1014*c*, integrally formed contact 912*d* is held in contact with cylindrical electrode 1014*d*, integrally formed contact 912*e* is held in contact with cylindrical electrode 1014*e* and integrally formed contact 912*f* is held in contact with cylindrical electrode 1014*f*.

When assembled, flexible lead 905 is held within cylindrical port 936 with collet 1112*b* adjacent coupling surface 1005. Flexible lead 905 is held within cylindrical port 936 by set screw 920.

When assembled, flexible lead 906 is held within cylindrical port 933 with collet 1112*c* held adjacent coupling surface 1003 by set screw 913. Cylindrical electrode 1015*a* is held in contact with integrally formed contact 910*a*. Similarly, cylindrical electrode 1015*b* is held in contact with integrally formed contact 910*b*, cylindrical electrode 1015*c* is held in contact with integrally formed contact 910*c*, cylindrical electrode 1015*d* is held in contact with integrally formed contact 910*d*, cylindrical electrode 1015*e* is held in contact with integrally formed contact 910*e* and cylindrical electrode 1015*f* is held in contact with integrally formed contact 910*f*.

Figures 11B, 11C:
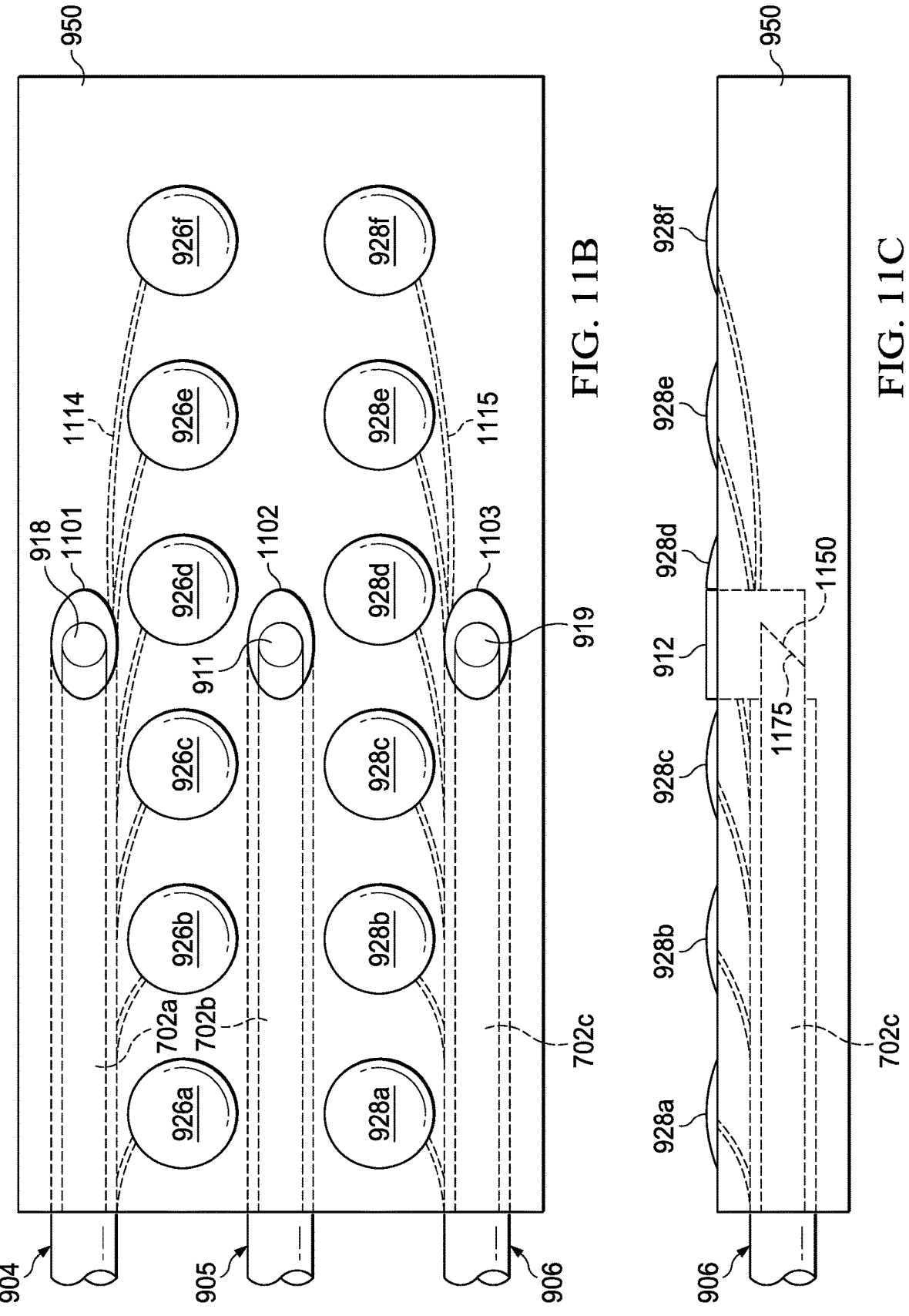
FIG. 11B is a plan view of a paddle shaped laminectomy lead of a preferred embodiment of a laminectomy lead contact.
FIG. 11C is a side view of a preferred embodiment of the paddle shaped laminectomy lead of the laminectomy lead contact.

Referring then to FIGS. 11B and 11C, paddle shaped laminectomy lead 950 will be further described. Paddle shaped laminectomy lead 950 is comprised of a flexible biocompatible sheet having components molded within it. Preferably the sheet is comprised of an inert silicon elastomer such as Silastic available from Dow Corning. In a preferred embodiment, paddle shaped laminectomy lead 950 further comprises transparent window 918, transparent window 911 and transparent window 919, attached to optical fiber assemblies 702*a*, 702*b*, and 702*c*, respectively. In each case, the transparent window comprises a generally cylindrical multi surface block of poly (methyl methacrylate) which is designed to fix the position the light collimator in the sheet and direct light toward the surface of the sheet. The surface of the window may be polished to retard biological fouling. In other embodiments, the light collimator may be so positioned in the sheet during manufacture that the transparent window is not used. Each of light collimators 1101, 1102, and 1103 in a preferred embodiment, is a cleaved optical fiber at 45° to the longitude and axis of the fiber. In a preferred embodiment, the beveled edge of each fiber includes a $TiO_2$ surface cladding which is comprised of nanoparticles embedded in a suitable biologically compatible epoxy. An example is shown at cleaved optical fiber 1150 on optical fiber 702*c* in FIG. 11C. During manufacture, the beveled edge of each fiber is positioned opposite of the electrode array plane an example of which is shown in FIG. 11C, at 1175.

Paddle shaped laminectomy lead 950 further comprises electrodes 926*a*, 926*b*, 926*c*, 926*d*, 926*e* and 926*f* and 928*a*, 928*b*, 928*c*, 928*d*, 928*e* and 928*f*. Each of electrodes 926*a*-926*f* and 928*a*-928*f* are exposed cylindrical metallic insets integrally molded into paddle shaped laminectomy lead 950. In a preferred embodiment, the exposed insets are convex to focus the electric field produced. In a preferred embodiment, electrodes are platinum or platinum alloy. One each of electrodes 926*a*-926*f* are connected to a single wire in electrode line bundle 1114. One each of electrodes 928*a*-928*f* is connected to a single wire in electrode line bundle 1117. The optical fibers are incorporated into the lead at the time of manufacture. The $TiO_2$ nanoparticle surface cladding is important in conversation of light intensity. Beveled edge 1175 projects the light path from the optical fiber perpendicularly in a single direction toward the surface of the electrode array.

Moving on to FIG. 12, laminectomy lead connector circuit 1200 will be described. VCC line 1012 is connected to LED 921. LED 921 is also connected to LFC 923*a* through bridge connection 1018*b*. LED 921 is connected to LFC 923*b* through bridge connection 1018*c*. LFC 923*a* is connected to Data B line 1006. LFC 923*a* is also connected to ground line 1008. LFC 923*b* is connected to Data A line 1010. LFC 923*b* is also connected to ground line 1008 through bridge connection 1018*a*. This configuration requires a nominal 6 milliamps forward current which is efficient to drive the LED. This configuration also requires a power overhead of approximately 6.7 microwatts assuming that a 30 Hz sampling frequency, 10 microsecond duty cycle and 3.7 volts supplied.

Referring again to FIG. 5, the general operation of percutaneous connector system 500 will be described.

In use, battery 509 supplies power to processor 514, LED 521 and LFC 523. The processor in a run state generates an LED signal which is translated by the LED into light energy. The light travels through flexible lead 506 where it is radiated through transparent tip 562 to impinge upon the spinal cord. Reflected light from the spinal cord enters transparent tip 520 where it is transmitted through flexible lead 504 and back to LFC 523. LFC 523 converts the reflected signal into a string of pulses of a frequency dependent upon light intensity. The frequency of these pulses is compared by the processor to a predetermined table in order to arrive at a voltage intensity and wave form for stimulation. The voltage intensity and wave form is transmitted through each of the six contacts on connector array 503 and six contacts on connector array 544, to contacts 510 and 512, respectively. The stimulation voltage and wave form reaches electrodes 504*a*-504*f* and 506*a*-506*f*, respectively, where it is delivered to the spinal cord to produce stimulation. Each of the contacts may be individually addressed for different a stimulation intensity and wave form.

Referring again to FIG. 9, the general operation of laminectomy lead connector system 900 will be described. Battery 909 provides power to processor 914, LED 921, and LFC 923*b* and 923*a*. In operation, the processor enters a run state where it sends power to LED 921. LED 921 converts the voltage to a light signal which travels through flexible lead 905 and is redirected by a light collimator through transparent window 911. Once transmitted the light is reflected from the spinal cord into each of transparent windows 918 and 919. The reflected light travels down each of flexible leads 904 and 906 to LFC's 923*b* and 923*a*, respectively. Each LFC translates the light intensity into a string of pulses with a specific frequency. These pulses are transmitted through flexible lead 925 and 927, respectively to processor 914. Processor 914 reads the pulses and compares them to a table to arrive at a stimulation intensity and wave form for each electrode. A voltage corresponding to this stimulation intensity and wave form is transmitted through connector arrays 903 and 944, respectively to contacts 910 and 912 where they are sent through the flexible leads to electrodes 926 and 928, respectively, to produce stimulation. In a preferred embodiment, each of the electrodes is individually addressable and can receive a different stimulation voltage and wave form.

The relationship between incident light and reflected light and the spinal cord in each case, is described in U.S. Pat. No. 10,045,697 to Wolf, the complete disclosure of which is incorporated herein by reference.

Referring then to FIG. 13A a processor state chart 1300 will be described. While each of the connectors eliminates the requirement for hardware changes to the IPG, it is necessary to change existing IPG firmware to repurpose up to four channels for use by the optoelectronics in the connectors. For example, one channel must be assigned as an electrical ground or current. As another example, one or two channels must be reassigned as digital input to accept data from the LFC devices. Also, one or two channels must act as current sources to drive the optical emitter and/or detectors. The process begins at stop state 1302. The processor is powered up at stop state 1302 and then is moved to run state 1304 by a control signal. Once in run state 1304 the processor periodically moves to measure light intensity state 1306 and then returns to run state 1304. In a preferred embodiment the processor changes between run state 1304 and measure light intensity state 1306 at a rate of approximately 10 Hz.

Moving to FIG. 13B, run state 1304 will be further described. At step 1310 the processor reads a stimulus value from a table using light intensity, will be further described. At step 1312, the processor translates the stimulus value into a signal as set out in the table. A stimulation voltage and waveform is then sent to each of the electrodes as previously described. Once the stimulation is sent, the processor returns to state 1310.

Figure 14:
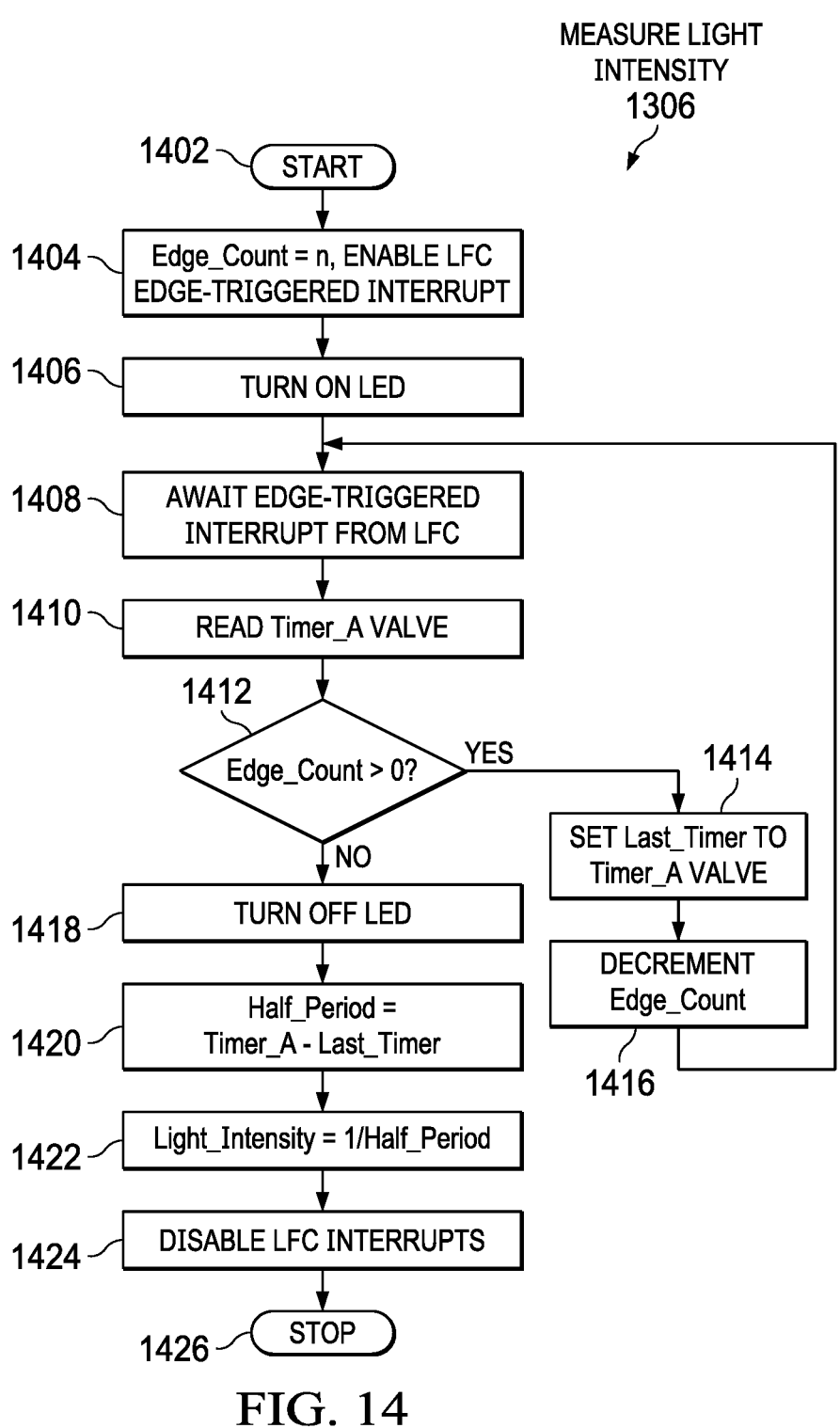
FIG. 14 is a flowchart of the "reach stimulus value" state of a preferred embodiment.

Referring then to FIG. 14, measure light intensity state 1306 will be further described. Assuming an industry standard Texas Instruments MSP430 microprocessor, the multiplexor of the processor is connected to the Data A and Data B contacts which are reconfigured to act as a set of digital inputs. The MSP430 timers A and B may be set to generate edge triggered interrupt requests in response to digital transitions on these inputs, thus providing a computationally efficient method of measuring frequency of the LFC's and thus reflected light intensity. The state is started at step 1402. At step 1404, an edge count value is set to an integer number. In a preferred embodiment N≥3 to allow for settling of the LFC. Timer A is started at zero to count forward. Timer A is a variable that represents 0 to FFFF hex and is the number of processor clock cycles between edge interrupts. At step 1404, the LFC edge triggered interrupt is also enabled.

At step 1406, the processor turns on the LED. At step 1408 the processor enters a wait state, while the timer runs waiting for an edge triggered interrupt from the LFC. When an edge triggered interrupt is received, at step 1410 the processor reads the value of timer A. At step 1412, the processor compares the value of the edge_count variable to zero. If the value is greater than zero, then the processor moves to step 1414. If the value is equal to zero, then the processor moves to step 1418. At step 1414, the timer A value is stored in the variable last_timer. At step 1416, the processor then decrements the integer value of edge_count, and returns to step 1408.

At step 1418, the processor turns off the LED. At step 1420, the processor executes a binary subtraction the value of timer A from the value of last timer to arrive at a value for half period. At step 1422, a value of light intensity is set to the reciprocal of half period. At step 1424, the processor disables the edge triggered interrupt. At step 1426, the processor returns a value of light intensity and stops.

Moving to FIG. 15, an example of a light intensity table 1500 will be described. At column 1502, a light intensity for a first LFC is shown by representative values of 1-10. These values may be different. At column 1506, an electrode voltage/waveform set of values is shown for electrode 1. Likewise in column 1508, 1510, 1512, 1514 and 1516 voltage waveform combinations are shown for electrode 2 through electrode 6. For embodiments with a greater or fewer number of electrodes, a greater or fewer number of columns will be provided.

At row 1518 the values for each electrode voltage and waveform are provided for a light intensity of 1. Similarly, for rows 1519, 1520, 1521, 1522, 1523, 1524, 1525, 1526 and 1527, values for voltage and wave form for light intensities 2-10 are shown. The voltage and wave form values are fed back to the processor at state 1310 to be used to generate a stimulation voltage and wave form at state 1312.

Referring to FIG. 16, the process 1600 for surgically inserting the IPG and laminectomy or percutaneous lead connector is described. At step 1602, the surgical laminectomy lead or percutaneous lead(s) are inserted in standard fashion and the exact procedural description is outside the scope of this document. At step 1604, a separate surgical incision is typically made in the skin of the buttock or flank to accept the IPG. At step 1606, a tunneling tool is passed subcutaneously from the electrode insertion site to the IPG site. At steps 1608 and 1610, the electrode lead ends are inserted into the lead connector and set screws are tightened. At steps 1612 and 1614, the flexible leads of the lead connector are then inserted into the IPG and the connections cinched using the IPG's integrated set screws. At steps 1616 and 1618, the excess lead length and lead connector are coiled behind the IPG and subsequently inserted into the IPG pocket. At step 1620, the incisions are then closed.

Turning to FIG. 17, method 1700 will be described. In the event that an existing SCS system needs servicing for battery replacement, at step 1702, the IPG pocket is surgically opened. At step 1704, the set screws are removed. At step 1706, the lead arrays are disconnected from the lead connector. At steps 1708, 1710 and 1712, a new IPG connected to a new lead connector assembly are then attached to the existing electrode lead arrays and the connection cinched with the lead connector set screws. At steps 1714 and 1716, the excess lead length and connector leads are coiled behind the IPG and these are reinserted into the IPG pocket. At step 1718, the incisions are closed. Thus, the optoelectronics are changed out at the same time as the IPG battery replacement.

The invention claimed is:

1. A method for connecting an IPG to a set of electrodes fixed on a first set of flexible leads by a lead connector comprising:

providing a connector body;

providing a set of connector ports within the connector body;

providing a set of internal contacts fixed to the connector body and operationally disposed within the set of connector ports;

providing a set of optoelectronics, supported by the connector body and operationally positioned in the set of connector ports;

providing a second set of flexible leads, connected to the connector body;

providing a first set of external contacts fixed on the second set of flexible leads;

providing a second set of external contacts fixed on the second set of flexible leads;

providing the second set of flexible leads further comprising a first set of conductors and a second set of conductors;

connecting the first set of conductors to the set of optoelectronics and to the first set of external contacts; and, connecting the second set of conductors to the set of internal contacts and to the second set of external contacts.

2. The method of claim 1, further comprising:

providing the set of optoelectronics as at least one photo emitter and at least one photo detector.

3. The method of claim 2, further comprising:

providing the at least one photo emitter as a near infrared LED.

4. The method of claim 3, further comprising:

providing the at least one photo detector as a light to frequency converter.

5. The method of claim 3, further comprising:

providing the set of optoelectronics as at least one lens adjacent one of the group of the at least one photo emitter and the at least one photo detector.

6. A method of connecting an IPG to a percutaneous lead connector system, comprising:

providing a connector body;

providing a first connection port in the connector body;

providing a second connection port in the connector body;

providing a first set of internal contacts in the first connection port;

providing a second set of internal contacts in the second connection port;

providing an optical emitter operationally positioned in the first connection port;

providing an optical detector operationally positioned in the second connection port;

providing a first flexible lead, having a first set of external contacts and a second set of external contacts, attached to the connector body adjacent the first connection port;

providing a second flexible lead, having a third set of external contacts and a fourth set of external contacts, attached to the connector body adjacent the second connection port;

providing a first set of conductors, inside the first flexible lead, connecting the optical emitter to the first set of external contacts;

providing a second set of conductors, inside the first flexible lead, connecting the first set of internal contacts to the second set of external contacts;

providing a third set of conductors, inside the second flexible lead, connecting the optical detector to the third set of external contacts; and, providing a fourth set of conductors, inside the second flexible lead, connecting the second set of internal contacts to the fourth set of external contacts.

7. The method of claim 6 further comprising:

providing a third flexible lead and a fourth flexible lead;

providing the third flexible lead as a first lead body with a first internal lumen;

providing the fourth flexible lead as a second lead body with a second internal lumen;

providing a first optical fiber assembly, operationally disposed in the first internal lumen;

providing a second optical fiber assembly, operationally disposed in the second internal lumen;

providing a first set of lead contacts and a first set of electrodes attached to an external surface of the third flexible lead and connected together by a first set of conductors within the first lead body;

providing a second set of lead contacts and a second set of electrodes attached to an external surface of the fourth flexible lead and connected together by a second set of conductors within the second lead body;

providing the first optical fiber assembly held adjacent the optical emitter by the connector body;

providing the second optical fiber assembly held adjacent the optical detector by the connector body;

providing the first set of lead contacts is held in contact with the first set of internal contacts by the connector body; and, providing the second set of lead contacts is held in contact with the second set of internal contacts by the connector body.

8. The method of claim 6, further comprising:

providing an IPG having a first set of IPG contacts and a second set of IPG contacts;

providing the first set of IPG contacts in contact with the first set of external contacts and the second set of external contacts; and, providing the second set of IPG contacts in contact with the third set of external contacts and the fourth set of external contacts.

9. The method of claim 7, further comprising:

providing the first optical fiber assembly as a $TiO_2$ surfaced negative axicon.

10. The method of claim 7, further comprising;

providing the first optical fiber assembly as a collet adjacent the optical emitter.

11. The method of claim 7, further comprising:

providing the first optical fiber assembly as a collet adjacent the optical detector.

12. The method of claim 6, further comprising providing the optical emitter as an LED.

13. The method of claim 6, further comprising:

providing the optical detector as an LFC.

14. A method of connecting an IPG to a percutaneous lead connector system, comprising:

providing a connector body;

providing a first connection port in the connector body;

providing a second connection port in the connector body;

providing a third connection port in the connector body;

providing a first photo detector operationally positioned in the first connection port;

providing a photo emitter operationally positioned in the second connection port;

providing a second photo detector operationally positioned in the third connection port;

providing a first set of internal contacts in the first connection port;

providing a second set of internal contacts in the third connection port;

providing a first flexible lead, having a first set of external contacts and a second set of external contacts, attached to the connector body;

providing a second flexible lead, having a third set of external contacts and a fourth set of external contacts, attached to the connector body;

providing the first set of external contacts is connected to the photo emitter and the first photo detector;

providing the second set of external contacts is connected to the first set of internal contacts;

providing the third set of external contacts is connected to the second photo detector and the photo emitter; and, providing the fourth set of external contacts is connected to the second set of internal contacts.

15. The method of claim 14 further comprising:

providing a fourth flexible lead, attached to a flexible paddle body, comprising a first optical fiber;

providing a fifth flexible lead, attached to the flexible paddle body, comprising a second optical fiber;

providing a sixth flexible lead, attached to the flexible paddle body, comprising a third optical fiber;

providing a flexible paddle body comprising a first set of electrodes and a second set of electrodes;

providing the second optical fiber positioned in the flexible paddle body to project light generally perpendicular to the flexible paddle body;

providing the first optical fiber and the third optical fiber positioned in the flexible paddle body to receive light generally perpendicular to the flexible paddle body;

providing the first set of electrodes in electrical contact with the first set of internal contacts;

providing the second set of electrodes in electrical contact with the second set of internal contacts;

providing the first optical fiber in optical contact with the first photo detector;

providing the second optical fiber in optical contact with the photo emitter; and, providing the third optical fiber in optical contact with the second photo detector.

16. The method of claim 14 further comprising:

providing an IPG having a first set of IPG contacts and a second set of IPG contacts;

providing the first set of IPG contacts in contact with the first set of external contacts and the second set of external contacts; and, providing the second set of IPG contacts in contact with the third set of external contacts and the fourth set of external contacts.

* * * * *